United States Patent
Woodhouse et al.

(10) Patent No.: US 11,359,233 B2
(45) Date of Patent: Jun. 14, 2022

(54) METHODS FOR LABELLING NUCLEIC ACIDS

(71) Applicant: Inivata Ltd., Cambridge (GB)

(72) Inventors: Samuel Woodhouse, Cambridge (GB); Tim Forshew, Stevenage (GB); Stefanie Viola Lensing, Cambridge (GB)

(73) Assignee: INIVATA LTD., Cambridge (GB)

( * ) Notice: Subject to any disclaimer, the term of this patent is extended or adjusted under 35 U.S.C. 154(b) by 0 days.

(21) Appl. No.: 16/330,352

(22) PCT Filed: Sep. 13, 2017

(86) PCT No.: PCT/EP2017/073064
§ 371 (c)(1),
(2) Date: Mar. 4, 2019

(87) PCT Pub. No.: WO2018/050722
PCT Pub. Date: Mar. 22, 2018

(65) Prior Publication Data
US 2019/0203283 A1    Jul. 4, 2019

(30) Foreign Application Priority Data
Sep. 13, 2016  (GB) ..................... 1615486

(51) Int. Cl.
| | | |
|---|---|---|
| *C12Q 1/6855* | (2018.01) | |
| *C12Q 1/6806* | (2018.01) | |
| *C12Q 1/6869* | (2018.01) | |
| *C12Q 1/68* | (2018.01) | |

(52) U.S. Cl.
CPC .............. *C12Q 1/6855* (2013.01); *C12Q 1/68* (2013.01); *C12Q 1/6806* (2013.01); *C12Q 1/6869* (2013.01); *C12Q 2525/117* (2013.01); *C12Q 2525/155* (2013.01); *C12Q 2525/179* (2013.01); *C12Q 2525/186* (2013.01); *C12Q 2525/191* (2013.01); *C12Q 2525/301* (2013.01); *C12Q 2535/122* (2013.01); *C12Q 2563/179* (2013.01)

(58) Field of Classification Search
None
See application file for complete search history.

(56) References Cited

FOREIGN PATENT DOCUMENTS

| | | | |
|---|---|---|---|
| WO | WO 2009/106308 | 9/2009 | |
| WO | WO 2009/133466 | 11/2009 | |
| WO | WO 2012/041857 | 4/2012 | |
| WO | WO 2013/138510 | 9/2013 | |
| WO | WO-2014118377 A2 * | 8/2014 | ........... C12Q 1/6844 |
| WO | WO 2015/134552 | 9/2015 | |

* cited by examiner

*Primary Examiner* — Samuel C Woolwine
(74) *Attorney, Agent, or Firm* — James S. Keddie; Bozicevic, Field & Francis LLP

(57) ABSTRACT

The invention relates to methods for labelling individual nucleic acid molecules present in a sample, comprising contacting the nucleic acid molecules with an adaptor or mixture of adaptors, wherein the adaptor or adaptors comprise one or more universal nucleotide bases and a ligation moiety at their 3' end, and ligating an adaptor to the nucleic acid of interest, wherein the adaptor is ligated to the nucleic acid molecules at the 3' end of the adaptor. A random tag is then generated in situ by conducting an extension reaction over the ligated adaptor. Methods of the invention may be used to detect genetic alterations or variants in any nucleic acid with high specificity and high sensitivity, including mutations in nucleic acids such as ctDNA, cfDNA, and in viral, microbiome and plant nucleic acids. Methods of the invention may also be used in detection and correction of errors introduced into nucleic acids during processing.

15 Claims, 8 Drawing Sheets
Specification includes a Sequence Listing.

METHODS FOR LABELLING NUCLEIC ACIDS

CROSS-REFERENCE TO RELATED APPLICATIONS

This application is a § 371 national phase of International Application No. PCT/EP2017/073064, filed on Sep. 13, 2017, which claims the benefit of United Kingdom Application No. 1615486.6, filed on Sep. 13, 2016, which applications are incorporated by reference herein.

INCORPORATION BY REFERENCE OF SEQUENCE LISTING

The Sequence Listing filed as a text file on Sep. 14, 2021, entitled "INIV-008_SEQ_LIST_ST25_Corrected" created on Sep. 14, 2021, and having a size of 12 KB is hereby incorporated by reference.

The invention relates to methods for labelling individual nucleic acid molecules present in a sample. Methods of the invention may be used to detect genetic alterations or variants in any nucleic acid with high specificity and high sensitivity, including mutations in nucleic acids such as ctDNA, cfDNA, and in viral, microbiome and plant nucleic acids. Methods of the invention may also be used in detection and correction of errors introduced into nucleic acids during processing.

BACKGROUND

Next-generation sequencing (NGS) has inherent error and amplification biases, decreasing the ability to detect genetic alterations at an allele frequency (AF) at or below 1% and making it difficult to distinguish alterations from processing errors. Several methods have been proposed to overcome these limitations. Tagging of NGS libraries with complex molecular barcodes has been used to detect NGS errors, these methods employ a fixed length of degenerate (mixed) bases coupled to sequencing adaptors that generate a high number of different tags, typically >100,000 possible combinations. The number of different tags present after sequencing can be used to estimate the number of different polynucleotides present initially. Molecular barcodes are synthesized as single-stranded oligonucleotides and can be attached by PCR, ligation or primer extension. To ensure that each nucleic acid present in a sample is labelled with an unique molecular barcode, it is necessary to generate a highly complex mix of barcodes, which can be a costly and time-consuming process that requires separate barcode synthesis reactions and pooling of tags. A low diversity tag of fixed length leads to inefficient sequencing as NGS/Illumina phasing calculations cannot be made, therefore a high degree of tag diversity is required. Further methods of identifying errors involve splitting the sample into multiple replicate processing steps and identifying changes that have occurred across multiple reactions. However, splitting the reaction increases costs, complexity and in some circumstances decreases assay sensitivity. Additionally, PCR/NGS generates errors based on sequence context and thus errors are not entirely random, this can lead to consistent errors within a given sequence. Bioinformatics tools trained on control sample sets can be used to filter out consistent NGS error, however they cannot account for random errors introduced by NGS processing, e.g., by PCR. In the above methods, an error introduced during the first copy/amplification of a nucleic acid of interest (NAOI) will be propagated through the reaction and could be identified as a "true" variant/alteration, even though it was an error that occurred during the PCR.

Molecular barcoding of nucleic acids is described in US20140066317, WO2015112974, WO2013142389, U.S. Pat. Nos. 8,835,358 and 8,481,292.

There remains a need for simple, cost-effective methods for labelling nucleic acids with a high degree of tag diversity, that reduce the likelihood of errors being introduced into the tag sequence during processing, and that allow true nucleic acid variants to be distinguished from errors introduced during processing of the tagged nucleic acid.

SUMMARY OF THE INVENTION

The present invention allows the in situ generation of molecular barcodes/tags. This is achieved by utilising adaptors having universal nucleotide bases that allow the incorporation of randomly generated tags in a nucleotide extension reaction.

Accordingly, in a first aspect of the invention, there is provided a double-stranded nucleic acid adaptor for tagging a nucleic acid of interest, the adaptor comprising two strands, wherein the first strand comprises one or more universal nucleotide bases and a ligation moiety at its 3' end, and wherein the second strand comprises a ligation block at its 5' end.

In a second aspect of the invention, there is provided an adaptor for tagging a nucleotide sequence, wherein the adaptor comprises one or more universal nucleotide bases and a ligation moiety at the 3' end.

In a third aspect of the invention, there is provided a mixture of adaptors of the invention, wherein the mixture comprises at least 2 different adaptors.

In a fourth aspect of the invention, there is provided a method of tagging a double-stranded nucleic acid of interest, comprising:
  a. contacting the nucleic acid of interest with an adaptor or mixture of adaptors of the invention; and
  b. ligating an adaptor to the nucleic acid of interest, wherein the adaptor is ligated to the nucleic acid of interest at the 3' end of the adaptor. A random tag is generated in situ by conducting an extension reaction over the ligated adaptor.

In a fifth aspect of the invention, there is provided a method for determining the sequence of a nucleic acid of interest, the method comprising:
  a. contacting the nucleic acid of interest with an adaptor or mixture of adaptors of the invention;
  b. ligating an adaptor to one or both ends of a nucleic acid of interest;
  c. extending the nucleic acid of interest over the ligated adaptor to generate a random tag on the nucleic acid of interest;
  d. amplifying the tagged nucleic acid of interest; and
  e. determining the sequence of the nucleic acid of interest.

In a sixth aspect of the invention, there is provided a method, the method comprising the steps of:
  a. providing a sample from a patient, said sample comprising a plurality of cell-free DNA (cfDNA) molecules; and
  b. determining the sequence of one or more of the cfDNA molecules according to a method of the invention as described herein.

In another aspect of the invention there is provided a method of diagnosing cancer, comprising:
  a. providing a sample from a patient, said sample comprising a plurality of ctDNAs;

b. determining the sequence of one or more of the ctDNAs according a method of the invention as described herein;
c. determining the presence or absence of one or more genetic alterations in the ctDNAs; and
d. determining the presence or absence of cancer based on the presence or absence of the one or more genetic alterations.

In another aspect of the invention there is provided a method of determining cancer remission or relapse, comprising:
a. providing a sample from a patient, said sample comprising a plurality of ctDNAs;
b. determining the sequence of one or more of the ctDNAs according to a method of the invention;
c. determining the presence or absence of one or more genetic alterations in the ctDNAs; and
d. determining cancer remission or relapse based on the absence or presence of the one or more genetic alterations.

In another aspect of the invention there is provided a method of detecting progression of cancer, comprising:
a. providing a sample from a patient, said sample comprising a plurality of ctDNAs;
b. determining the sequence of one or more of the ctDNAs according to a method of the invention as described herein;
c. determining the presence or absence of one or more genetic alterations in the ctDNAs, or determining a change in the abundance of the one or more genetic alterations;
d. optionally comparing the results from step (c) to the results for the same patient using a sample obtained at a previous point in time; and
e. determining a progression of cancer based on the presence or absence of the one or more genetic alterations, or based on a change in the abundance of the one of more genetic alterations.

In another aspect of the invention there is provided a method of determining the presence of residual cancer, comprising:
a. providing a sample from a patient, said sample comprising a plurality of ctDNAs;
b. determining the sequence of one or more of the ctDNAs according to a method of the invention as described herein;
c. determining the presence or absence of one or more genetic alterations in the ctDNAs; and
d. determining the presence of residual cancer based on the presence or absence of the one or more genetic alterations.

In a further aspect of the invention there is provided a method of stratifying a microbial population, comprising:
a. obtaining a sample comprising a plurality of microbial nucleic acids of interest;
b. determining the sequence of one or more of the microbial nucleic acids of interest according to a method of the invention as described herein;
c. mapping the sequence reads obtained in step b to a reference genome or genomes; and
d. stratifying the microbial population according to the identified microbes.

In a still further aspect of the invention, there is provided a method of error correcting nucleic acid sequence reads, the method comprising:

a. providing a dataset comprising a plurality of sequence reads from a sample, each sequence read comprising a PCR counter, the sequence of a nucleic acid of interest, and a tag;
b. grouping sequence reads by tag or by tag and NAOI sequence similarity and aligning the sequence reads; and
c. correcting errors in the sequence reads, if necessary, to provide a consensus sequence for each originating nucleic acid of interest.

In a further aspect of the invention, there is provided a method of counting sequencing reads comprising:
a. providing a dataset comprising a plurality of sequence reads from a sample, each sequence read comprising a PCR counter, the sequence of a nucleic acid of interest, and a tag;
b. grouping sequence reads by tag or by tag and NAOI sequence similarity and aligning to generate a consensus sequence for each originating nucleic acid of interest; and
c. counting the number of originating nucleic acids of interest starting molecules to determine the copy number of the original NAOI.

In a further aspect of the invention there is provided a method of treating cancer, comprising
a. providing a sample from a patient, said sample comprising one or more cell-free nucleic acid molecules;
b. determining the sequence of one or more of the cell-free nucleic acid molecules according to a method of the invention as described herein;
c. determining the presence or absence of a genetic alteration in the cell-free nucleic acid molecules;
d. selecting a cancer treatment regimen for the patient according to the presence or absence of a genetic alteration in the one or more cell-free nucleic acid molecules; and
e. administering said treatment to the patient.

In a further aspect of the invention there is provided a method of selecting a treatment regimen for a cancer patient or a patient suspected of having cancer, comprising:
a. providing a sample from a patient, said sample comprising one or more cell-free nucleic acid molecules;
b. determining the sequence of one or more of the cell-free nucleic acid molecules according to a method of the invention as described herein;
c. determining the presence or absence of a genetic alteration in the cell-free nucleic acid molecules; and
d. selecting a cancer treatment regimen for the patient according to the presence or absence of a genetic alteration in the cell-free nucleic acid molecules.

In a further aspect of the invention there is provided a method of predicting a patient's responsiveness to a cancer treatment, comprising
a. providing a sample from a patient, said sample comprising a plurality of cell-free DNA (cfDNA) molecules;
b. determining the sequence of one or more of the cfDNA molecules according to a method of the invention as described herein;
c. determining the presence or absence of a genetic alteration in the cell-free nucleic acid molecules; and
d. predicting a patient's responsiveness to a cancer treatment according to the presence or absence of a genetic alteration.

In a further aspect of the invention there is provided a mixture or composition comprising a plurality of adaptors of the invention, and one or more nucleic acids of interest.

In a further aspect of the invention there is provided a kit of parts comprising one or more adaptors of the invention and instructions for use.

In the top-left panel, each sequence (from top to bottom SEQ ID NOs:23, 23, 23, 24, 24, 23, 25, 24, 26, 27) has a common tag (CGCTACG), 50% of reads (SEQ ID NO:23) have 1 PCR counter sequence (CGTAGCG) and 50% of reads (from top to bottom SEQ ID NOs:26, 24, 25) have one of 3 PCR counter sequences (CCGATAG, TTAGCTA or AATGATC) the sequence with only one PCR counter sequence contains an error. The multiple copies of the parental strand, each with one of the 3 different PCR counter sequences, show the true sequence of the original NAOI (SEQ ID NO:34).

In the bottom-left panel, each sequence (from top to bottom SEQ ID NOs:28, 29, 29, 29, 30, 31, 32, 32, 32, 33) has a common tag (TTGACGA) 90% of reads (from top to bottom SEQ ID NOs:29, 30, 31, 32, 33) have one of 5 PCR counter sequences (TGATCAT, TTAGCTA, CGTATCG, AGTGATC or CTTAGCG) and 10% of reads (SEQ ID NO:28) have 1 PCR counter sequence; a true variant NAOI is detected in all copies of the parental strand. An error present in the 10% of reads that have 1 PCR counter sequence (GTAGCAT) is error corrected to provide a consensus sequence for the variant (SEQ ID NO:35).

Figure 4:
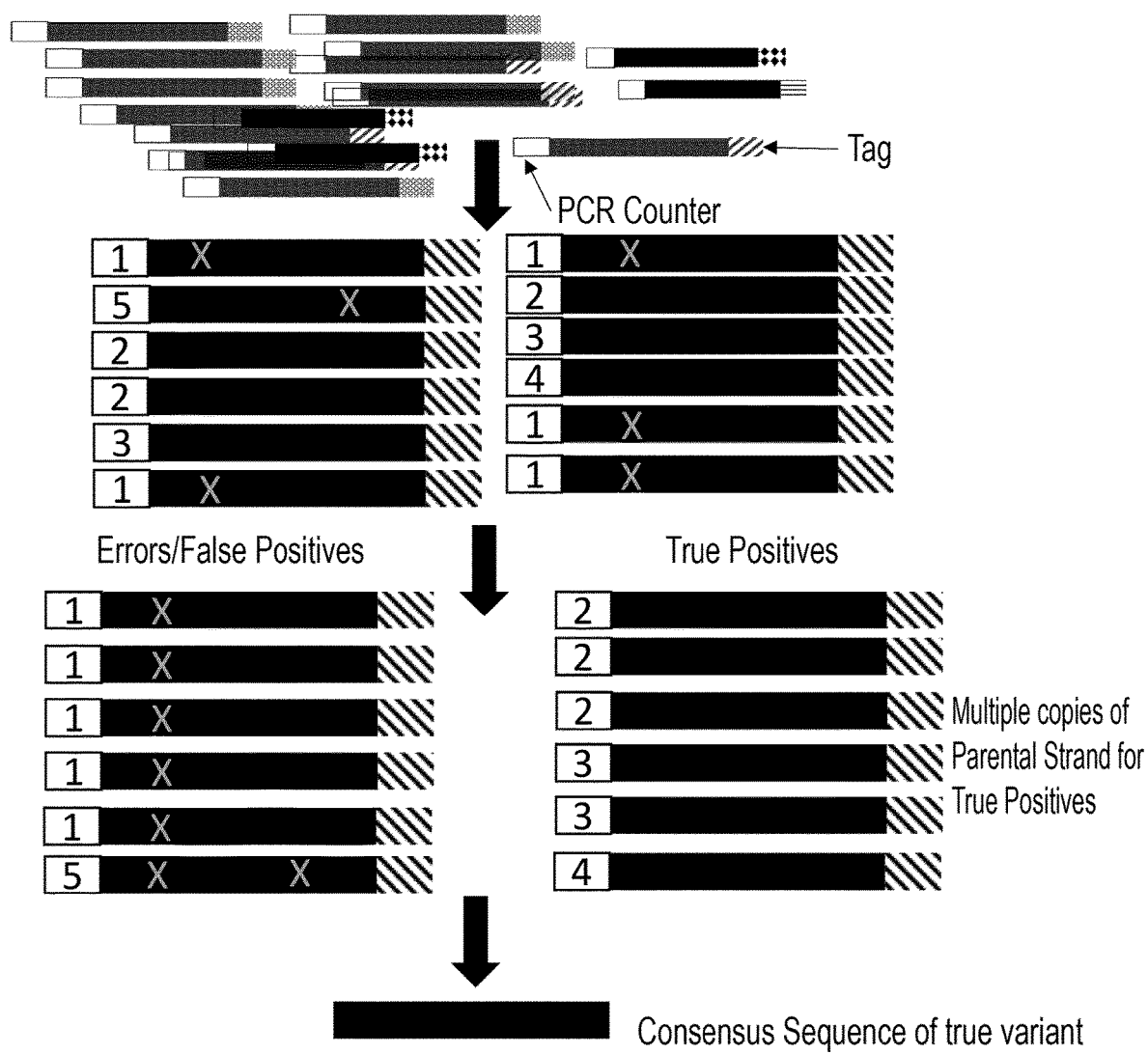
Figure 5A:
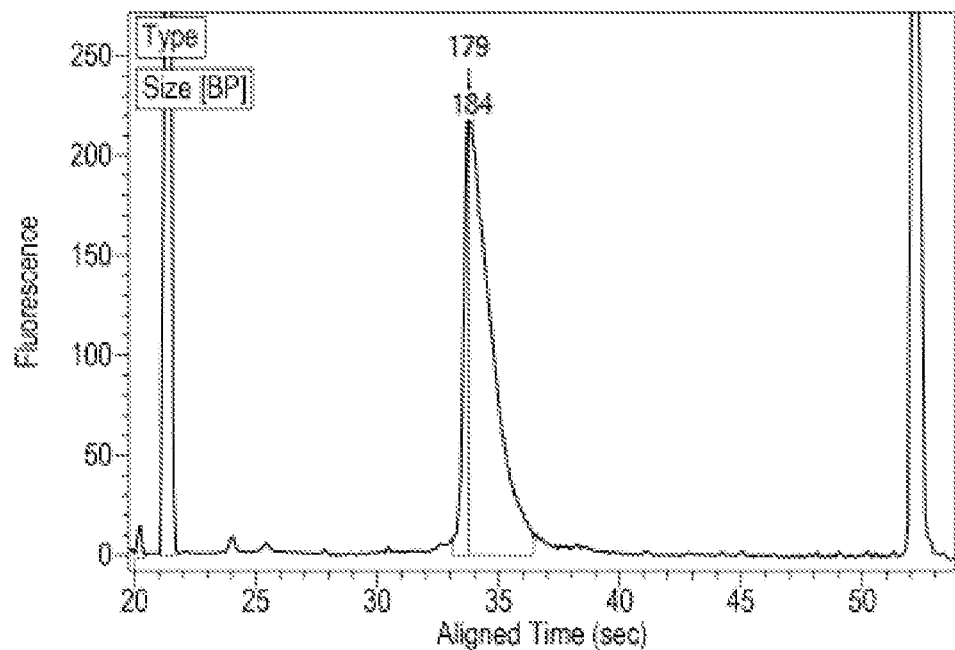
Figure 5B:
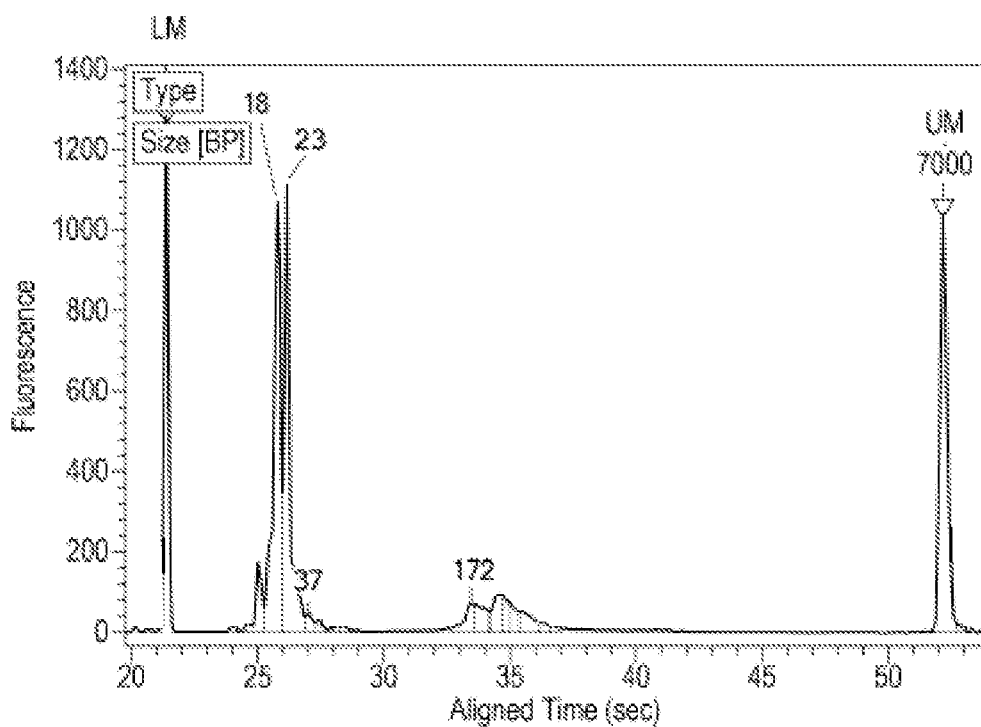
Figure 5C:
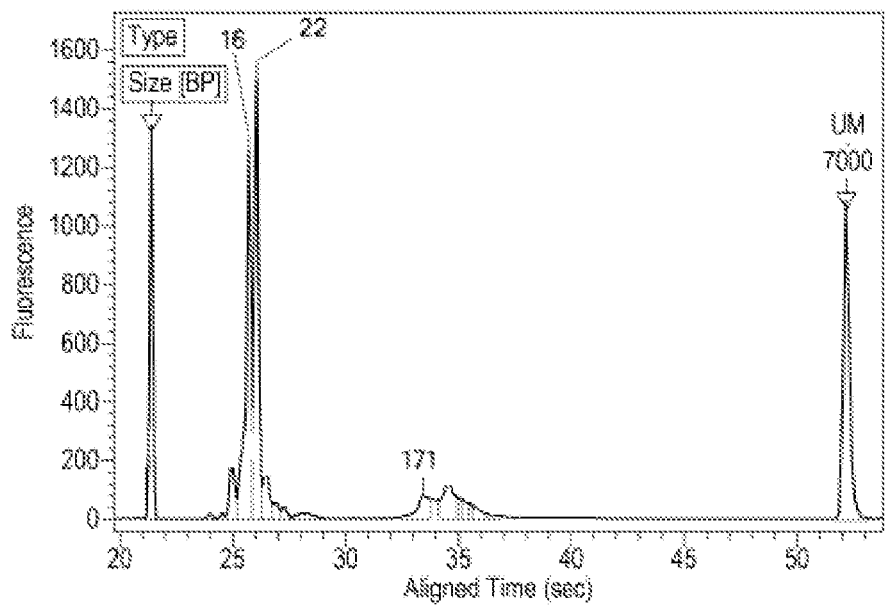
Figure 5D:
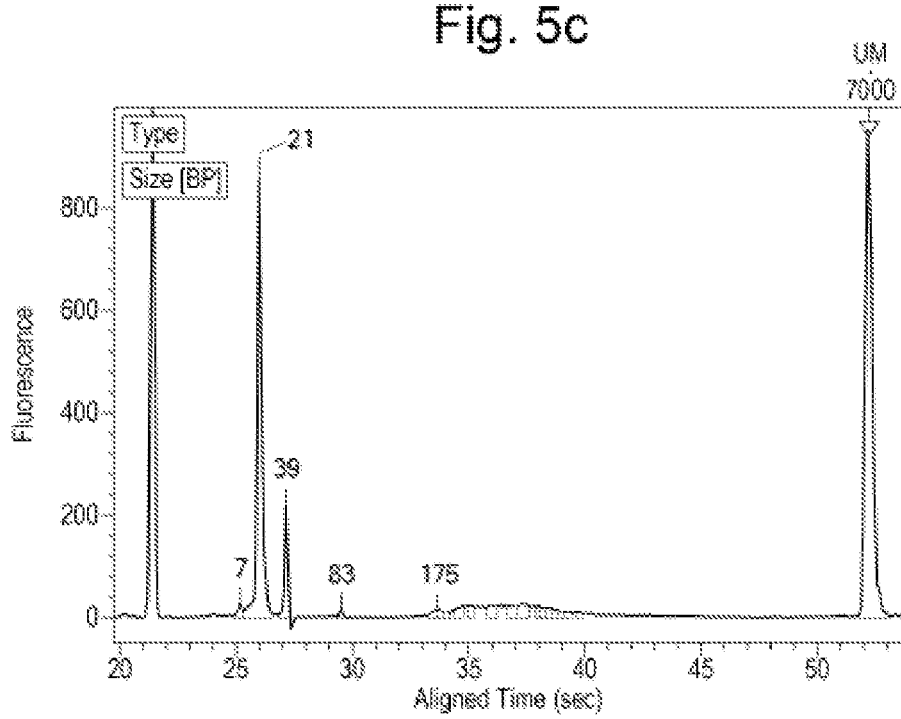
Figure 5E:
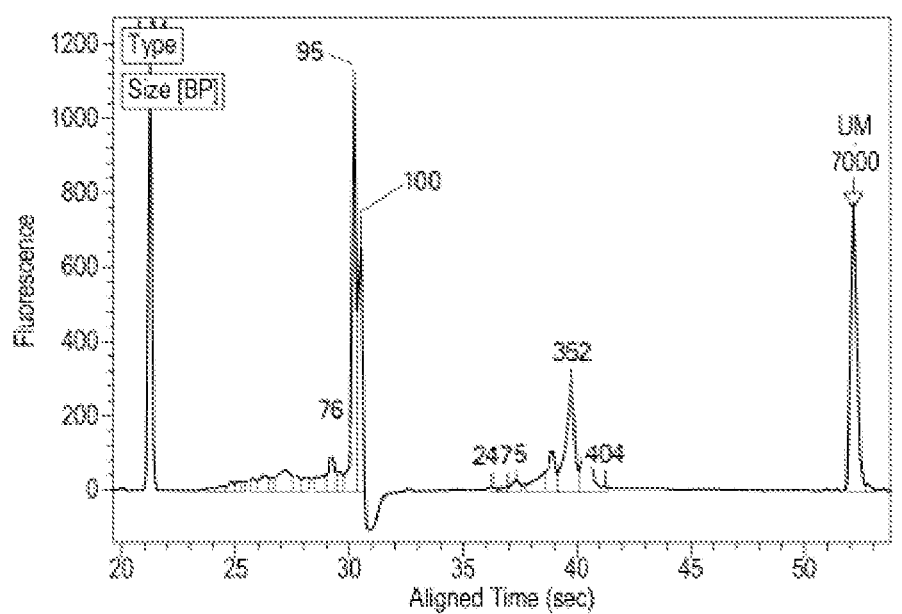

FIG. 4—A scheme for error correcting sequencing reads to distinguish between true variants and errors introduced during processing. The scheme uses PCR counters generated by extension over an extension adaptor strand comprising universal bases that is ligated to an original NAOI molecule strand.

FIG. 5—Results. Capillary electrophoresis of DNA at intervals throughout the workflow. The X axis denotes the amount of product, and the Y-axis denotes the size of the product.

a) DNA of a single fragment length, used as starting material.

b) DNA following the ligation of extension adaptors.
c) DNA following Taq extension.
d) DNA following the additional ligation of Illumina adaptors.
e) DNA following amplification.

DETAILED DESCRIPTION OF THE INVENTION

Current molecular barcoding methods use a plurality of complex adaptors that each contain a unique molecular barcode. The adapters are ligated randomly onto nucleic acids of interest (NAOI) and used as molecular identifiers for individual nucleic acid molecules. In contrast, methods of the invention use an adaptor comprising universal bases (inosines are used as an example), with an extension reaction being performed to generate barcode tags. Universal bases allow the incorporation of A, G, C or T randomly into the strand that is synthesised. Only the extended strand is used as an identifier; thus the barcode tag is generated by the extension reaction after attaching an adaptor (extension adapter) as described herein to the nucleic acid of interest and not by a ligation reaction using of a mix of barcoded adaptors. Therefore, only one adaptor is required, yet this can generate a high complexity of molecular tags. A complex library of adaptors can therefore be generated in situ without having to provide a pre-prepared library of unique molecular tags. Errors and cross-contamination of barcodes do not occur as the molecular tag is generated only after the adaptor has been ligated and extended.

As discussed in more detail below, the invention also provides a means of measuring the number of times a parental strand is copied by way of a "PCR counter". The PCR counter is generated by repeated reading of the parental strand, since the barcode produced will differ each time by virtue of the universal bases in the ligated extension adaptor. Standard molecular barcoding and NGS sequencing techniques would not be able to identify errors introduced when the first copy of the NAOI is generated. The PCR counter of the invention can be used to improve error correction as only the correct NAOI sequence will have multiple PCR counters associated with it, and therefore true genetic alterations and variations can be distinguished from errors introduced during processing. This PCR counter provides a further significant advantage over the prior art.

Extension Adaptors

The present invention provides adaptors (referred to as extension adaptors) that are specifically designed to allow the incorporation of a barcode (also referred to as a tag herein) into a NAOI by an extension reaction. The extension adaptors may be double or single-stranded. Double-stranded extension adaptors comprise two strands that are hybridised together. Hybridisation may be determined as hybridisation under stringent conditions. Stringent hybridising conditions are known to the skilled person, and are chosen to reduce the possibility of non-complementary hybridisation. Examples of suitable conditions are disclosed in Nucleic Acid Hybridisation: A Practical Approach (B. D. Hames and S. J. Higgins, editors IRL Press, 1985). For example, stringent hybridisation conditions include an aqueous environment containing about 30 mM magnesium sulfate, about 300 mM Tris-sulfate at about pH 8.9, and about 90 mM ammonium sulfate at about 60-68° C., or equivalents thereof. Single-stranded extension adaptors may be in the form of a stem loop or hairpin loop, or may have a tertiary structure, to increase stability of the molecule. Preferably the extension adaptors are double stranded.

In one embodiment of the invention, the extension adaptor is double-stranded and comprises two strands. The first strand comprises one or more universal nucleotide bases and has a ligation moiety at its 3' end. The second strand comprises a ligation block at its 5' end. The two strands hybridise together under stringent conditions. In another embodiment, the extension adaptor is a single-stranded adaptor, wherein the adaptor comprises one or more universal nucleotide bases and a ligation moiety at the 3' end. Additional features of the adaptor discussed herein apply equally to both the double and single-stranded embodiments, unless specified otherwise or dictated by the context. The extension adaptors are DNA or RNA extension adaptors, but are preferably DNA adaptors.

For double-stranded extension adaptors, these preferably further comprise a ligation moiety at the 5' end of the universal base-contain strand to allow ligation of sequencing adaptors and a ligation block at the 3' end of the complementary strand to prevent blunt-ended ligation to a second adapter (adapter dimerization). However, these additional ligation moieties and ligation blocks are not strictly necessary. Said moieties can be phosphate groups (these can act as both a ligation block if attached at the 3' end, or a ligation moiety if attached at the 5' end), although other groups known to the skilled person could be used. Single-stranded extension adaptors preferably comprise a ligation block at the 3' end (e.g. a 3' phosphate group) to prevent blunt-ended ligation to a second adapter (adapter dimerization), although again this is not essential.

"Nucleic acid of interest" or "NAOI" refers to nucleic acids that can be tagged using the extension adaptors of the invention. NAOIs include cell-free DNA (cfDNA), in particular circulating tumour DNA (ctDNA) but also cell free fetal DNA. Alternatively, any nucleic acids for which the sequence or presence is to be determined may be considered a NAOI. Generally the NAOI is double-stranded, although the invention is also applicable to single-stranded NAOI. If the NAOI is single stranded, it is preferable for this to be converted to a double-stranded NAOI before tagging and sequencing. Means for converting a single-stranded NAOI of interest to a double-stranded NAOI are known to the skilled person. The term "originating NAOI" refers to an original or parental NAOI molecule present in a sample (or purified therefrom). In methods of the invention progeny versions of the originating NAOI are generated, after tagging, by amplification and by sequencing.

In order to undergo tagging and sequencing, the NAOI may be at least 25 base pairs in length. In some embodiments, the NAOI may be from 25 to 100,000 base pairs in length, from 25 to 50,000 base pairs in length, from 25 to 10,000 base pairs in length, from 25 to 1000 base pairs in length, from 50 to 500 base pairs in length in length, from 100 to 250 base pairs in length, or from 100 to 200 base pairs in length. In order for the NAOI to be tagged and sequenced, the NAOI may be fragmented to an appropriate size (for example between 100 and 200 base pairs in length). Indeed, the NAOI may be an entire genome that is fragmented to an appropriate length to allow tagging and sequencing to take place. As discussed below, the NAOI may be from any suitable source, including a human, plant or microbial source, depending on the method being undertaken. Most commonly, the NAOI will be a human NAOI. A sample comprising NAOIs may comprise a mixture of NAOIs from a plurality of different sources.

"Universal nucleotide base" and "universal base" refer to bases that are able to hybridise to more than one type of nucleotide under stringent conditions. Generally, any base lacking hydrogen bond donor or acceptor functionalities that can sufficiently stabilize duplex DNA by intra-strand base interactions may act as a universal base, without destabilizing the duplex. A universal base preferably pairs indiscriminately in any sequence context, or at least does not have a strong preference for a particular type of base under stringent conditions. Examples of universal bases that can be used in the invention include 2'-deoxyinosine (inosine) and derivatives thereof, nitroazole analogues and derivatives thereof, hydrophobic aromatic non-hydrogen-bonding bases and derivatives thereof, 3'-nitropyrrole bases and derivatives thereof (for example 3'-nitropyrrole CE phosphoramidite), nitroindole bases and derivatives thereof (for example 4-, 5- and 6-nitroindole CE phosphoramidite) as well as derivatives such as 5-nitroindole-3-carboxamide, 2'-deoxynucleoside and derivatives thereof as well as K-2'-deoxyribose, P-2'-deoxyribose, 2'-deoxyisoguanine and 2'-deoxynebularine. Inosine bases may be preferred. The extension adaptors of the invention may comprise a single type of universal base (such as inosine), or the extension adaptors may comprise a mixture of more than one type of universal base. "Type" in this context refers to the specific species of universal base, for example each of 2'-deoxyinosine (inosine), 3'-nitropyrrole CE phosphoramidite, 4-, 5- and 6-nitroindole CE phosphoramidite and 2'-deoxynucleoside are all different types (or "species") of universal base.

Universal base analogues with no pairing bias and no alteration in stability are reviewed in Loakes D. (2001) Survey and summary: The applications of universal DNA base analogues. Nucleic Acids Res, 29(12): 2437-2447, the contents of which are incorporated by reference herein.

When inosine is used, the preferential bias for incorporation of cytosine can be overcome by adapting the nucleotide composition in the extension mix to bias the reaction away from dC. Typically, dATP is present at a significantly higher concentration for the A-tailing reaction, and so this bias will result in lower incorporation of dCTP in the tag. Alternatively, the extension reaction can be performed in isolation and an adapter lacking the nucleobase guanine can be used; thus making it possible to completely omit dCTP from the extension reaction. In such embodiments, only dTTP, dGTP and dATP will be present in the extension reaction and available for incorporation opposite the universal base.

When universal bases such as nitroindole and 5-nitroindole-3-carboxamide are used, it may be necessary to use existing and new bespoke polymerases that are able to incorporate dNTPs and extend across such types of universal base (as discussed in, for example, Loakes, et al (2009) J Am Chem Soc. 131(41) Evolving a polymerase for hydrophobic base analogues).

"Non-universal nucleotide base" and "non-universal base" refer to nucleotide bases that only pair with one type of base under stringent conditions, or has a strong preference for only one type of base. Non-universal bases include the standard "natural" bases A, T, C, G and U. The IUPAC system of nomenclature is used herein, nucleobases are represented by the first letters of their chemical names: A (Adenine), T (Thymine), C (Cytosine), G (Guanine) and U (Uracil). Generally, in the case of a double-stranded extension adaptor, the second strand does not comprise any universal bases and instead comprises only standard non-universal bases; this is to promote hybridisation of the two strands to each other and stability of a double stranded adapter, or hybridisation of the relevant parts of a single stranded adaptor, such as single stranded adaptors in the form of a hairpin.

"Ligation moiety" refers to any nucleotide sequence capable of ligation. Exemplary ligation moieties include overhangs and blunt ends. Overhangs may be an overhang of one or more bases. Single base overhangs are preferred, and a single T base overhang is most preferred in the extension adapter. The overhangs can be universal or non-universal bases. The overhang is preferably a non-universal base overhang. Ligation moiety may also refer to a 5' phosphate group. If an extension adaptor comprises an overhang, the extension adaptor may optionally further comprise a phosphothioate linkage between the universal base containing strand and the overhang. A phosphothioate bond stops the adapter being digested by enzymes that have exonuclease activity "Ligation block" refers to any sequence or moiety that prevents ligation of the nucleic acid to another nucleic acid or nucleotide base. Any suitable ligation block can be used, for example a non-phosphorylated nucleotide, an inverted dT, a C3 spacer, or a 3' phosphate group. A non-phosphorylated nucleotide is preferred.

The first strand of extension adaptors of the invention may comprise at least 1, 2, 3, 4, 5, 6, 7, 8, 9, 10, 11 or 12 universal bases, in particular from 1 to 20 universal bases, from 5 to 15 universal bases, or from 8 to 12 universal bases. Generally, the adaptors should comprise a sufficient number of universal bases to provide a sufficient variation in possible barcode tag sequences. Therefore, at least 4 universal bases may be preferred in order to ensure sufficient complexity in the resulting barcodes. However, fewer universal bases could be used, in particular for a mixture of extension adaptors having different sequences with the universal bases interspersed with non-universal bases and the universal bases occurring at various positions in the extension adaptor. Therefore, in some contexts extension adaptors with a first strand comprising a mixture of universal and non-universal bases are preferred. Hence in embodiments in which the extension adaptor is double-stranded, the first strand may comprise universal and non-universal bases.

In some embodiments, the first strand of an extension adaptor of the invention does not comprise any non-universal bases (with the possible exception of the ligation moiety, which is preferably a single non-universal base overhang). However, extension adaptors with a first strand comprising universal and non-universal bases may be preferred as the presence of the non-universal bases may serve to increase the stability of the extension adaptors. For example, for double-stranded adaptors, the presence of non-universal base pairs in the first strand increases the stability of the molecule as it promotes hybridisation of the two strands together. Similarly, for single-stranded extension adaptors, such as those in a hairpin or stem loop formation, the presence of non-universal base pairs increases the stability of the molecule as it promotes hybridisation between the complementary parts of the molecule.

For those extension adaptors comprising both universal and non-universal bases in the first strand for double stranded adaptors or only strand for single stranded adaptors, the universal bases in the extension adaptor may be contiguous or non-contiguous. A non-contiguous arrangement of universal bases, in particular a non-contiguous arrangement of inosines (where the universal bases such as inosines are interspersed with one or more non-universal bases) may be preferred to confer increased stability. Other universal bases (such as nitroindole) may be placed in a contiguous or non-contiguous arrangement to confer increased stability. In addition, the positions of the universal bases may be varied between extension adaptors in a given pool to provide additional combinations of possible barcodes for identifying nucleic acids of interest.

The overall length of the extension adaptor can vary depending on the design. For example, the extension adaptor may be at least 6, at least 8 or at least 10 nucleotides in length (or base pairs, in the case of a double-stranded extension adaptor). In one embodiment, the extension adaptor is from 6 to 100, from 6 to 50, from 10 to 50, from 15 to 50, or from 20 to 45 nucleotides in length (or base pairs, in the case of a double-stranded extension adaptor). A length of 25 to 40 nucleotides or base pairs is preferred. Generally the adaptors might not be more than 45 nucleotides in length, unless in embodiments in which the adaptors further comprise other sequences, such as index sequences or sequencing adaptors, in which case they may be longer than this.

In one embodiment, the arrangement of nucleotides in the first strand of a double-stranded extension adaptor or in the only strand of a single-stranded extension adaptor can be as follows, in a 5' to 3' order:

[$X_1$]-[$X_2$]-[$X_3$]-[ligation moiety]

wherein:
$X_1$=one or more non-universal bases;
$X_2$=one or more universal bases, optionally further comprising one or more non-universal bases; and
$X_3$=one or more non-universal bases.

Such an arrangement may be beneficial, as the one or more non-universal bases at each end of $X_2$ will increase the stability of the molecule by promoting hybridisation (to the second strand, in the case of a double-stranded extension adaptor, or to the complementary section of the molecule in the case of a single-stranded extension adaptor).

In one embodiment, $X_2$ is from 4 to 50 nucleotide bases in length, or from 4 to 40 nucleotide bases in length, or from 4 to 35 nucleotide bases in length and/or wherein $X_2$ comprises at least 2, at least 3, at least 4, at least 5, at least 6, at least 7, at least 8, at least 9 or at least 10 universal bases. Preferably, $X_2$ comprises at least 4 universal bases. In one embodiment, $X_2$ comprises from 8 to 12 universal bases. In a more preferred embodiment, $X_1$ and $X_3$ are both a single non-universal base. In one embodiment, $X_1$ is from 1 to 5 nucleotides, $X_2$ is between 15 and 40 nucleotides, and $X_3$ is from 1 to 5 nucleotides. In some embodiments, $X_2$ is from 4 to 98 nucleotide bases in length, or from 4 to 48 nucleotide bases in length, or from 8 to 48 nucleotide bases in length, or from 18 to 43 nucleotide bases in length In one embodiment, the extension adaptor is double-stranded, comprising two strands hybridised to each other. The first strand comprises at least 4 universal nucleotide bases and has a single non-universal base overhang as a ligation moiety at its 3' end. The second strand comprises a non-phosphorylated ligation block at its 5' end. The adaptor is preferably between 10 and 50 base pairs in length, preferably between 25 and 40 base pairs in length. In some embodiments of the invention, at least about 10%, at least about 20%, or at least about 30% of the bases in the first strand of the adaptor for double stranded adaptors or in the only strand of the adaptor for single stranded adaptors are universal bases.

In use, a single arrangement of bases, ligation block and ligation moieties might be used. For example, all extension adaptors used in a given reaction might be identical. Alternatively, a mixture of two or more types of extension adaptor (of different sequence) may be used to increase the diversity of barcode tags that are generated. For example, in one embodiment of the invention there is provided a mixture of extension adaptors, wherein the mixture comprises at least 2 different adaptors. The adaptors differ in their sequence, for example such that the positions of the one or more universal bases are not identical in all extension adaptors in the mixture, or alternatively the "constant" part of the adaptor (consisting of non-universal bases) may differ between adaptors to cause the relative positions of the universal bases to shift (hence providing more than one "type" of extension adaptor). In such mixtures, the extension adaptors may have two or more arrangements of universal and non-universal bases (i.e. sequences), but preferably the ligation moieties and ligation blocks will not differ between adaptors, i.e., each adaptor will have a common ligation moiety and a common ligation block. The mixtures may comprise more than 2 different types of adaptors. For example, the mixture may comprise at least 2, at least 3, at least 4, at least 5, at least 6, at least 7, at least, 8, at least 9, or at least 10 different adaptors. A mixture of at least 4 different adaptors is preferred. In such mixtures, it is preferred that each adaptor has at least 4 universal bases, where the arrangement (i.e., position) of universal and non-universal bases in each type of adaptor in the mixture is different, and/or wherein the arrangement of non-universal bases differs to cause a shift in the relative locations of the universal bases. Preferably, in a mixture of different types of adaptors, no one type of adaptor has all its universal bases in the same position as another type of adaptor in the mixture. However, certain residue positions may have a universal base in the same place in more than one type of adaptor, thus the position of a universal base may be fixed in the tag. For example, in a mixture of 4 different types of adaptors A, B, C and D, each adaptor having at least 4 universal bases, the positions of the universal bases could be:

Adaptor type A may have universal bases at the $3^{rd}$, $5^{th}$, $7^{th}$ and $9^{th}$ positions (counting from the 5' end of the adaptor);
Adaptor type B may have universal bases at the $2^{nd}$, $3^{rd}$, $6^{th}$, $8^{th}$ and $9^{th}$ positions;
Adaptor type C may have universal bases at the $3^{rd}$, $7^{th}$, $10^{th}$ and $12^{th}$ positions;
Adaptor type D may have universal bases at the $4^{rd}$, $6^{th}$, $8^{th}$, $9^{th}$ and $12^{th}$ positions.

Another example of a mixture is as follows, where the arrangement of non-universal bases causes the relative positions of the universal bases to shift with respect to the other members of the mixture:

Adaptor type A may have universal bases at the $9^{th}$, $12^{th}$, $15^{th}$ and $20^{th}$ positions (counting from the 5' end of the adaptor);
Adaptor type B may have universal bases at the $10^{th}$, $13^{th}$, $16^{th}$ and $21^{st}$ positions;
Adaptor type C may have universal bases at the $11^{th}$, $14^{th}$, $17^{th}$ and $22^{nd}$ positions;
Adaptor type D may have universal bases at the $12^{th}$, $15^{th}$, $18^{th}$ and $23^{rd}$ positions.

Alternatively, the positions of the universal bases may be fixed and the sequence of the non-universal bases may change. In some embodiments, a combination of these two types of variations may be used. The context will determine the level of heterogeneity in barcodes that is needed and hence the extension adaptor or extension adaptor pool complexity.

The precise design of the adaptors is not fixed and the skilled person would understand how to create a mixture of different types of adaptors that can provide a sufficient number of different barcodes, as required by the context.

The number of possible tag sequences that can be generated using the extension adaptors or mixtures of extension of the invention can be at least 10, at least 50, at least 100, at least 500, at least 1000, at least 5000, at least 10,000, at least 50,000, or at least 100,000. Preferably, the extension adaptor or mixture of extension adaptors is capable of producing at least 1,000 different barcodes.

In the case of a mixture of double-stranded extension adaptors, the adaptors may differ in the sequence of the second strand. Alternatively or additionally, the adaptors may differ in the sequence of their first strand.

The adaptors, including the mixtures of adaptors, may be provided in aqueous solution.

In some embodiments, the extension adapter that contains the universal base can also contain a sequencing adaptor (or partial sequencing adaptor). This may be referred to as a one-step ligation method, since a single ligation can be used to attach both the extension adaptor to generate the barcode on the NAOI and the sequencing adaptor to allow sequencing of the NAOI. In such embodiment, the sequencing adaptors will be at the 5' end of the extension adaptor for single stranded adaptors, and for ds adaptors, the sequencing adaptor is at the 5' end of the universal-base containing strand, and the 3' end of the complementary strand. The sequencing adaptors may be partial Illumina adapter sequences. Generally, to allow next generation sequencing to take place, different ends of the same strand of the NAOI need to be differentially labelled. Therefore, the extension adaptors comprising sequencing adaptors may be present as a pool of 2 different types, wherein some adaptors have one type of sequencing adaptor, and other adaptors have a different type of sequencing adaptors. To take the Illumina sequencing adaptors as an example, the two sequencing adaptors could be P5 and P7 adaptors. When a combination of different adaptors is used in the "one step ligation" embodiments, 50% of all tagged molecules would by chance receive only P5 or only P7 adapters thus sequencing would not be possible. Therefore, 50% of the molecules would be lost, although there would be a smaller loss of NAOI due to inefficient ligation as only one ligation reaction is required.

The extension adaptors may be provided as a pool of extension adaptors. The pool of extension adaptors may comprise at least 4 different types of extension adaptor of the invention. In some embodiments, all of the extension adaptors may be of the same length (or differing in length by only up to 3 nucleotides) but differ according to the arrangement of universal and/or non-universal bases.

Importantly, the pool of adaptors as provided and used herein does not need to be as complex as barcode pools of the prior art, since the methods themselves provide the in situ heterogeneity that allows NAOIs to be uniquely tagged. Therefore, the pool of adaptors used in the invention generally does not include more than 50 different types of adaptors (i.e. there are up to 50 different sequences in the pool of adaptors).

The extension adaptors have a known sequence as they are artificially produced. Hence although the barcode tags are degenerate and produced at random, the extension adaptors are not degenerate since their sequence is known.

Methods of Tagging Nucleic Acids

The present invention also provides methods of tagging NAOIs using the extension adaptors of the invention.

In the case of a double-stranded extension adaptor, the method comprises:
a. contacting the nucleic acid of interest with a double-stranded extension adaptor or mixture of double-stranded extension adaptors of the invention; and b. ligating a double-stranded extension adaptor to the nucleic acid of interest, wherein the adaptor is ligated to the nucleic acid of interest at the 3' end of the first strand of the adaptor but is not ligated at the 5' end of the second strand of the adaptor. The second strand of the adaptor is not ligated to the nucleic acid of interest.

In the case of a single-stranded extension adaptor, the method comprises:

a. contacting the nucleic acid of interest with a single-stranded extension adaptor or mixture of single-stranded extension adaptors of the invention; and b. ligating a single-stranded extension adaptor to the nucleic acid of interest, wherein the adaptor is ligated to the nucleic acid of interest at the 3' end of the adaptor. The adaptor is not ligated at the 5' end of the adaptor.

Ligated NAOIs (having an extension adapter ligated to one or each end of the NAOI) obtainable by such methods are also provided.

After the adaptor is ligated to the NAOI, an extension reaction in the 5' to 3' direction adds a barcode tag to the NAOI. This in situ generation of a molecular barcode is advantageous over the art since it does not require the provision of a previously generated pool of molecular barcodes. Instead, a new population of barcodes can be generated de novo each time the method is carried out. Since the extension adaptor comprises one or more universal bases, multiple different barcode tags are generated by the extension reaction, allowing the majority (e.g. at least 50%, at least 60%, at least 70%, at least 80% or at least 90%) of different NAOIs to be tagged with unique barcodes to enable their later identification. Increasing the complexity of the extension adaptors (for example by increasing the number of universal bases and/or using a mixture of extension adaptors having different sequences) increases the number of barcodes that can be generated and increases the chance of each NAOI being labelled with a unique tag. It is not necessary for all NAOIs in a sample to be labelled with a unique tag, since the sequence of the NAOI can also be used to distinguish between different starting molecules. However, a higher diversity of barcode tags is generally preferred.

Given the design of the extension adaptors, ligation between the adaptor and the nucleic acid of interest occurs only between the 5' end of the strands of the nucleic acid of interest and the 3' end of the adaptor, to generate a contiguous sequence. Thus, in the case of double-stranded extension adaptors, the second strand of the adaptor is not ligated to the NAOI.

Figure 3:
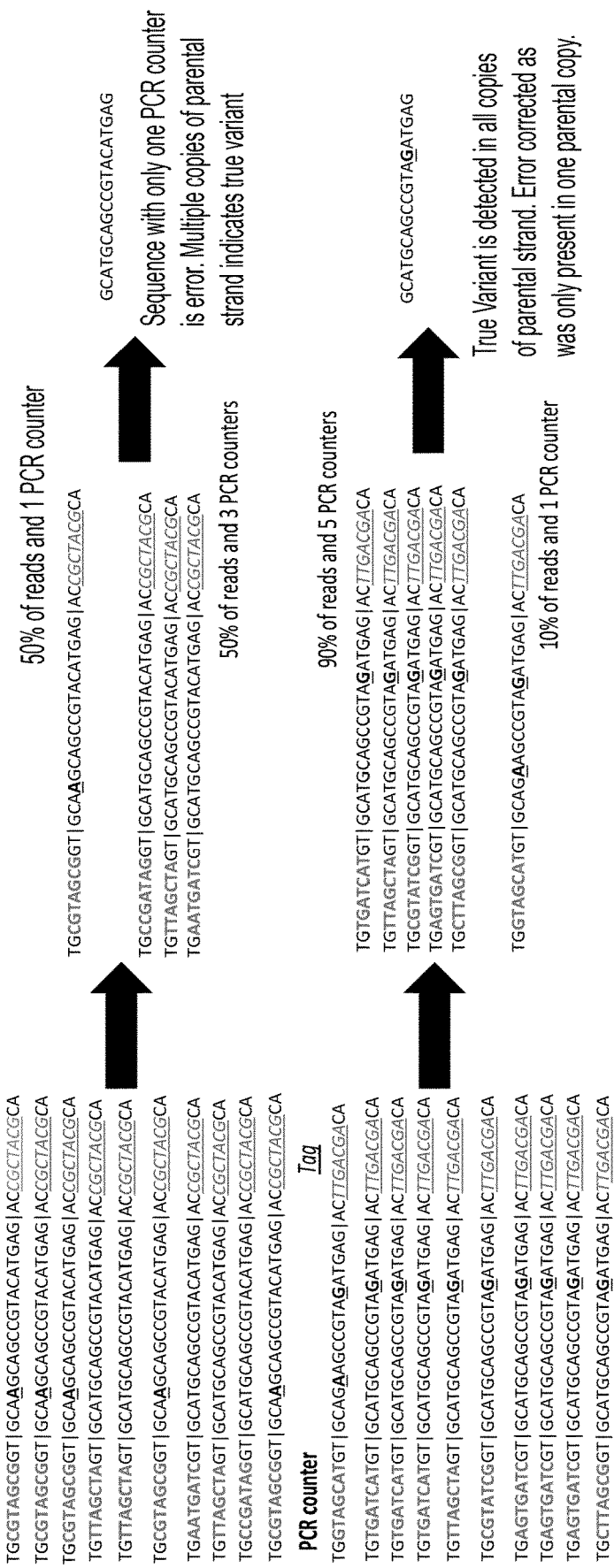
FIG. 3—A scheme for error correcting sequencing reads to distinguish between true variants and errors introduced during processing. The scheme uses tags and PCR counters generated by retention of the extension adaptor comprising universal bases that is ligated to the original NAOI molecule. Molecules are grouped based on tag and NAOI sequence similarity. Molecules sharing the same NAOI sequence but different tag are independent starting molecules. PCR counters are shown in bold, true variant residues and errors are shown in bold and underlined, tag sequences are shown in italic and underlined.

Ligation may occur at one or preferably each end of the NAOI. As discussed further below, when the tagged NAOI is later amplified using PCR, the product of the extension reaction at one or each end of the molecule is used as a tag to identify the sequence when the sequence reads are analysed (since after the first round of PCR, the sequence of the tag is fixed). However, the strands of the original starting NAOI molecule to which the extension adaptor with universal bases has been ligated will remain in the reaction mixture and will generate a new amplicon for each cycle of the PCR. Since the sequence of the amplicon will not be fixed (because the presence of the universal bases), this part of the sequence can be used to provide information on the number of times a parental (i.e. originating NAOI at the start of the PCR reaction) molecule was used as a template. Referring to FIG. 3, this demonstrates that the barcode at the 3' end of each strand of the tagged NAOI is fixed for each cycle of PCR. However, a new PCR counter is generated for each new copy of the parental strand that is generated during PCR. In FIG. 3, the amplicons are grouped according to the sequence of the PCR counter. It is more likely than not that the parental strand will be copied correctly, thus errors generated by incorrectly copying of the parental strand can be detected, because the incorrect sequence will have fewer different PCR counters associated with it. Methods of the prior art cannot detect such errors, because if a parental strand is copied incorrectly, in particular at an early cycle of the PCR, that incorrect sequence may account for most of the sequence reads for that NAOI. The present invention overcomes this problem.

Referring now to FIG. 4, it can be seen that in this example, an error is introduced in the $1^{st}$ and $5^{th}$ cycles of PCR. Standard molecular barcoding and NGS sequencing techniques would not be able to identify these errors generated early in the PCR process as errors, and may instead consider these errors to be variants in the sequence of the NAOI. Importantly, the "PCR counter" of the invention can be used to improve error correction, since only true sequences (or variants/alterations, in the case of mutations in the NAOI, such as cancer mutations) will have sufficiently high numbers of associated PCR counter sequences. If the number of PCR counters associated with a given sequence read is too low, this may be an indication that the sequence contains an error introduced by the PCR reaction, and should be ignored. As shown in the right-hand side of the bottom part of FIG. 4, only the correct NAOI sequence has multiple PCR counters associated with it, and therefore it can be distinguished from errors introduced during processing.

To promote ligation of the NAOI to the extension adaptor, the nucleic acid of interest may comprise a ligation moiety at the end of one or each of the strands of the nucleic acid of interest (or such moieties may be added). The ligation moiety may be an overhang that is complementary to the 3' ligation moiety on the extension adaptor to enable association and ligation of the two molecules together. If no such ligation moiety is present on the NAOI, then the method may further comprise the step of adding a ligation moiety to the end of one or each of the strands of the nucleic acid of interest. Depending on the nature of the ligation moiety, it may be present (or added) to the 3' end of one or each of the strands of the NAOI. For example, a single base overhang at the 3' end of a strand of a NAOI will promote ligation of the 3' end of a double stranded extension adaptor to the 5' end of the complementary strand of the double stranded NAOI. (Of course, double stranded extension adaptors of the present invention are not fully complementary given the presence of universal bases, but they are sufficiently complementary to allow hybridisation, in particular they are complementary with respect to all non-universal bases, with the exception of any overhangs). Ligation moieties used on the NAOI are preferably overhangs, more preferably a G or A overhang, and further preferably a single A base overhang. Generally, the ligation moiety is not a universal base.

The NAOI may be processed in other ways prior to ligation. For example, the NAOI may have undergone fragmentation and/or end repair. In some embodiments of the invention, the methods may include a step of fragmenting the NAOI and/or end repair of the NAOI. The NAOI may also be phosphorylated at the 5' end(s) and/or have an A-tail added at the 3' end(s). In some embodiments, depending on the method used, the step of end-repairing the NAOI may also provide a suitable A-tail (for example when using a polymerase to end-repair the NAOI). Other processing steps include amplification of the NAOI, for example using whole genome amplification, to increase the overall amount of the NAOI in the reaction.

Ligation reactions can be carried out according to any suitable method known to the skilled person, although generally ligation enzymes (ligases) will be used. The ligase may be a DNA or RNA ligase. In some embodiments, the ligase is a T4 DNA ligase.

After ligation, an extension reaction using a polymerase generates the barcode tag in situ. The barcode tag is synthesised using the extension adaptor sequence as a template. For those positions at which a universal base is present in the extension adapter sequence, the sequence of the barcode tag is generated randomly, because universal bases are able to pair with more than one type of non-universal base. For example, inosine is capable of forming a base pair with any of A, T, C, G or U, and so for each inosine, any of these standard bases may be incorporated. Inosine exhibits a slight preference for pairing with C, and so the random barcode tag may be generated semi-randomly (rather than completely at random). This usually will not present a problem, especially when the design of the extension adaptor or mixture of extension adaptors is sufficient to produce many different barcode sequences, despite the slight preference of inosine to pair with C. In any event, the bias for incorporation of C can be reduced by using a lower concentration of dC in the reaction mixture relative to the other nucleotides.

Extension reactions can be carried out according to any suitable method known to the skilled person, although generally extension enzymes (for example polymerases) will be used. The polymerase may be a DNA or RNA polymerase. In some embodiments, the polymerase is a Taq DNA polymerase.

Tagged NAOIs obtainable according to the methods described herein are also provided.

In some embodiments, the methods of the invention may also comprise purification of the reaction mixture, e.g., to remove un-ligated extension adaptors (and/or un-ligated asymmetric adaptors). This can be achieved according to any suitable method known to the skilled person. For example, purification may comprise the use of magnetic SPRI beads. Such beads are paramagnetic (magnetic only in a magnetic field) and this prevents them from clumping and falling out of solution. Each bead is made of polystyrene surrounded by a layer of magnetite, which is coated with carboxyl molecules. These reversibly bind DNA in the presence of a crowding agent (for example polyethylene glycol (PEG) and salt (20% PEG, 2.5M NaCl)). PEG causes the negatively-charged DNA to bind with the carboxyl groups on the bead surface. As the immobilization is dependent on the concentration of PEG and salt in the reaction, the volumetric ratio of beads to DNA is critical. Magnetic SPRI beads can be used for size separation, for example to distinguish between tagged NAOI and shorter, un-ligated extension adaptors that remain in the reaction mixture. DNA fragment size affects the total charge per molecule with larger DNAs having greater charges; this promotes their electrostatic interaction with the beads and displaces smaller DNA fragments. The size of fragments eluted from the beads (or that bind in the first place) is therefore determined by the concentration of PEG, and this in turn is determined by the mix of DNA and beads. A 50 ul DNA sample plus 50 ul of beads will give a SPRI:DNA ratio of 1. As this ratio is changed the length of fragments binding and/or left in solution also changes. The lower the ratio of SPRI:DNA the longer the final fragments will be at elution. Smaller fragments (i.e., the un-ligated extension adaptors) retained in the buffer can be discarded. The precise method used for a given reaction mixture can be determined by the skilled person who will be familiar with such purification methods.

Other methods of purification, e.g., for removing the extension adaptor, include the use of a single-strand nuclease to digest any un-ligated extension adaptors. Such a method is generally only suitable when single-stranded extension adaptors are being used.

After ligation of the extension adaptor(s) to the NAOI and generation of the barcode tags using an extension reaction, the resulting tagged NAOI may undergo further processing. For example, a further ligation moiety may be added to the 3' end of one or each of the strands of the NAOI. The polymerase used to generate the barcode tag may incorporate such a ligation moiety itself. For example, Taq DNA polymerase may generate a single A base overhang at the 3' end of the extended strand(s) of the NAOI.

After tagging, methods of the invention may further comprise a step of differentially labelling the strands of the tagged NAOI. This enables the two strands to be distinguished from one another following subsequent PCR amplification and sequencing.

Differential labelling of the strands of the tagged NAOI can be achieved according to any method known to a skilled person, although generally this will be achieved using asymmetric adaptors, such as Y-stem adaptors. Asymmetric adaptors are double-stranded adaptors having a complementary section and a non-complementary section. The complementary section is a section where the two sequences are complementary and hybridised together. This end of the asymmetric adaptor is ligated to the tagged NAOI. The non-complementary section of the asymmetric adaptor acts as the label for the two strands. The different sequences of the two strands in the non-complementary section of the asymmetric adaptor allow the incorporation of a different label on each of the two strands of the tagged NAOI. Suitable Y-stem adaptors include P7/P5 adaptors (Illumina), although the present invention is not limited to the use of these specific adaptors. Preferably, asymmetric labelling of the tagged double-stranded NAOI occurs at each end of the tagged double-stranded NAOI molecule.

The asymmetric adaptors may comprise an index sequence. The index sequence can be used to identify the sample in subsequent sequencing and analysis.

Any extension adaptors remaining in the reaction mixture after addition of the asymmetric adaptor may compete with the asymmetric adaptors for ligation. Therefore, steps may be taken to reduce this interference, for example by removing the extension adaptors using purification methods known in the art (such as Ampure XP), introducing the asymmetric adaptor in excess, so that the asymmetric adaptors out compete the extension adaptor for ligation, G-Tailing the NAOI and using C-Tailed extension adaptors (during the first ligation), then A-Tailing and using T-Tailed Y-stem adaptors, using single-stranded extension adaptors and treating with exonuclease to remove the single-stranded adaptors after the first ligation and extension, and/or incorporating a RNA or uracil nucleotide into the extension adaptor and removing the un-ligated adaptor after extension.

In some embodiments of the invention, the ligation moieties on the extension adaptor and asymmetric adaptor are single base overhangs, but to avoid competition between the adaptors, the single base overhangs on the extension adaptors and asymmetric adaptors are different from one another. For example, in one embodiment, the ligation moiety on the extension adaptor is a single C base overhang, and the ligation moiety on the asymmetric adaptor is a single T base overhang.

After the NAOIs have been tagged (using the extension adaptors) and optionally labelled (using the asymmetric adaptors), the NAOIs may be amplified, for example using PCR, to enable further processing and analysis. Therefore, the asymmetric adaptors may additionally enable a PCR reaction to take place, for example by providing a site complementary to primers used in the PCR reaction.

A library of tagged and labelled NAOIs obtainable by the methods of the invention is also provided herein. After ligation of the asymmetric adaptors, there may also be a step of purification, e.g., to remove un-ligated adapters.

In one embodiment of the invention, the method of tagging a nucleic acid comprises:
 a. contacting the nucleic acid of interest with a single-stranded extension adaptor or mixture of single-stranded extension adaptors of the invention;
 b. ligating a single-stranded extension adaptor to the nucleic acid of interest, wherein the adaptor is ligated to the nucleic acid of interest at the 3' end of the adaptor, to provide a tagged NAOI;
 c. optionally purifying the sample to remove excess (un-ligated) adaptors;
 d. ligating asymmetric adaptors to each end of the tagged NAOI to provide a tagged and labelled NAOI; and
 e. optionally purifying the sample to remove excess (un-ligated) adaptors.

Note the single-stranded adaptor is not ligated to the NAOI at its 5' end.

In one embodiment of the invention, the method of tagging a nucleic acid comprises:
 a. contacting the nucleic acid of interest with a double-stranded extension adaptor or mixture of double-stranded extension adaptors of the invention;
 b. ligating a double-stranded extension adaptor to the nucleic acid of interest, wherein the adaptor is ligated to the nucleic acid of interest at the 3' end of the strand containing one or more universal bases, to provide a tagged NAOI;
 c. optionally purifying the sample to remove excess (un-ligated) adaptors;
 d. ligating asymmetric adaptors to each end of the tagged NAOI to provide a tagged and labelled NAOI; and
 e. optionally purifying the sample to remove excess (un-ligated) adaptors.

Note the second strand of the adaptor is not ligated to the nucleic acid of interest.

The purification of steps e. above is generally more important than the purification of steps c. above, to avoid interference with a subsequent amplification by PCR.

In both embodiments above, an extension reaction is performed to generate the tag having a random sequence in situ.

The sample is then ready for further processing, in particular amplification and sequencing.

Methods of Sequencing Nucleic Acids

The present invention also provides methods for determining the sequence of a nucleic acid of interest, the method comprising:
 a. contacting the nucleic acid of interest with an adaptor or mixture of adaptors of the invention;
 b. ligating an adaptor to one or both ends of a nucleic acid of interest;
 c. extending the nucleic acid of interest over the ligated adaptor to generate a random tag on the nucleic acid of interest;
 d. amplifying the tagged nucleic acid of interest; and
 e. determining the sequence of the nucleic acid of interest.

The invention also provides a method for determining the sequence of a nucleic acid of interest, the method comprising:
 a. providing a NAOI with a random tag obtained by a method of tagging a NAOI of the invention;
 b. amplifying the tagged nucleic acid of interest; and
 c. determining the sequence of the nucleic acid of interest.

The invention also provides a method for determining the sequence of a nucleic acid of interest, the method comprising:
 a. providing an amplicon prepared by tagging and subsequent amplification of a NAOI according to a method of tagging of the invention as described herein; and
 b. determining the sequence of the nucleic acid of interest.

The invention also provides sequencing reads obtained according to any such methods of determining the sequence of a nucleic acid of interest.

In methods of the invention, e.g., for determining the sequence of a NAOI, the steps of ligating the extension adaptor and generation of a random tag can be carried out as discussed above. The NAOI may have already undergone processing (e.g., fragmentation and/or end repair) as discussed above, or such processing steps may be part of the method. Purification of the reaction mixture as described above may also take place.

Amplification is generally conducted using PCR. In preferred methods of the invention, NAOI are tagged with extension adapters of the invention and provided with asymmetric adapters, for example asymmetric adapters may be ligated onto the tagged NAOI, prior to amplification. When the NAOI has been both tagged and asymmetrically labelled, the PCR may use primers directed against the asymmetric portion of the asymmetric adaptors. The primers may comprise a sample identifier (for example an index sequence) to enable the sample to be identified during subsequent analysis.

In some embodiments, the methods of the invention may comprise a step of target enrichment. The target enrichment step, if present, is generally conducted after the NAOI is tagged and asymmetrically labelled, and preferably after the tagged and labelled NAOI has been amplified. Target enrichment can be carried out according to any method known to the skilled person, for example as discussed in Mamanova et al., "Target-enrichment strategies for next-generation sequencing", 2010, *Nature Methods,* 7:111-118 or Bodi et al., "Comparison of Commercially Available Target Enrichment Methods for Next-Generation Sequencing", 2013, *J Biomol Tech.,* 24(2):73-86, each of which are incorporated herein by reference. Target enrichment allows the subsequent sequencing and analysis steps to focus on a genetic region of interest. Methods of target enrichment include RNA probe enrichment (for example Agilent™ SureSelect™ target enrichment), DNA probe enrichment (for example NimbleGen™ SeqCap EZ Choice™ enrichment) or array-based enrichment (for example NimbleGen™ array capture enrichment). Enrichment when used in the methods of the invention is a separate step of the method and does not occur as part of the ligation and extension reactions.

The methods of the invention may comprise a number of amplification reactions. For example, and most commonly, amplification of the NAOIs may be carried out after the NAOIs are tagged and asymmetrically labelled. In addition, amplification may be carried out prior to tagging to increase the amount of starting molecules. If target enrichment is conducted, a subsequent amplification may also be employed in the method. Clonal amplification can be undertaken as part of the step of determining the sequence of the NAOI.

Determining the sequence of the tagged, labelled, amplified and optionally enriched NAOI can be carried out according to any suitable method known to the skilled person. However, given the number of NAOIs that will be analysed in any given method, next-generation sequencing (NGS) methods are preferred. Next-generation sequencing is also referred to as high-throughput sequencing and massively-parallel sequencing in the art, and is known and understood by the skilled person. A review of next-generation sequencing techniques is provided in Goodwin et al., "Coming of age: ten years of next-generation sequence technologies", 2016, *Nature Reviews,* 17:333-351.

The next-generation sequencing employed by the present invention may be selected from the group consisting of sequence-by-synthesis (SBS), sequencing-by-ligation (SBL) and long-read sequencing (LRS). The sequencing-by-synthesis may be selected from the group consisting of cyclic reversible termination SBS and single-nucleotide addition SBS. The long-read sequencing may be selected from the group consisting of single-molecule LRS and synthetic long-read LRS. Methods of sequence determination using sequencing-by-synthesis may be preferred.

Accordingly, in some embodiments of the invention, the method may further comprise localising tagged nucleic acids of interest to discrete sites. The discrete sites may comprise a solid or semi-solid substrate. The method may also comprise hybridizing or immobilising the tagged nucleic acids of interest to the solid or semi-solid substrate and clonally amplifying the localised and tagged NAOIs.

The NAOIs may be contained in or derived from a sample from a patient. In some embodiments, the sample is a biological sample obtained from a subject, or a sample containing nucleic acid of interest that is extracted from a biological sample obtained from a subject. The sample can be a tissue sample, for example a surgical sample. Preferably the sample is a liquid biopsy sample, such as blood, plasma, serum, urine, seminal fluid, stool, sputum, pleural fluid, ascetic fluid, synovial fluid, cerebrospinal fluid, lymph, nipple fluid, cyst fluid, or bronchial lavage. In some embodiments the sample is a cytological sample or smear or a fluid containing cellular material, such as cervical smear, nasal brushing, or esophageal sampling by a sponge (cytosponge), endoscopic/gastroscopic/colonoscopic biopsy or brushing, cervical mucus or brushing.

Many of the above samples can be obtained non-invasively, and can therefore be taken regularly without great risk or discomfort to the subject. Methods of the invention may comprise a step of obtaining a sample from a patient. Alternatively, the methods may be carried out on samples previously obtained from a patient (i.e., ex vivo/in vitro methods). In one embodiment of the invention, samples and/or NAOIs of interest are obtained by dialysis.

Samples may be obtained from patients suspected of having a particular disease or condition, such as cancer. Such a disease or condition can be diagnosed, prognosed, monitored and therapy can be determined based on the methods, systems and kits described herein. Samples may be obtained from humans or from animals, such as a domesticated animal, for example a cow, chicken, pig, horse, rabbit, dogs, cat, or goat. Usually, a sample will be derived from a human.

To obtain a blood sample, any technique known in the art may be used, e.g., a syringe or other vacuum suction device. A blood sample can be optionally pre-treated or processed prior to tagging and analysis. Examples of pre-treatment steps include the addition of a reagent such as a stabilizer, a preservative, a fixant, a lysing reagent, a diluent, an anti-apoptotic reagent, an anti-coagulation reagent, an anti-thrombotic reagent, magnetic property regulating reagent, a buffering reagent, an osmolality regulating reagent, a pH regulating reagent, and/or a crosslinking reagent. In addition, plasma may be obtained from the blood sample, and the plasma be used in the subsequent analysis.

When obtaining a sample from a human or an animal (e.g., blood sample), the amount can vary depending upon human or animal size and the condition being screened. In some embodiments, up to 50, 40, 30, 20, 10, 9, 8, 7, 6, 5, 4, 3, 2, or 1 mL of a sample is obtained. In some embodiments, 1-50, 2-40, 3-30, or 4-20 mL of sample is obtained. In some embodiments, more than 5, 10, 15, 20, 25, 30, 35, 40, 45, 50, 55, 60, 65, 70, 75, 80, 85, 90, 95 or 100 mL of a sample is obtained.

A sample may be processed prior to undergoing further analysis. Such processing steps may comprise purification (for example removal of cells and/or debris from the sample) or extraction or isolation of the NAOI from the sample.

The sample might not always be a patient sample, but instead could be a sample obtained from the environment, for example when testing for the presence or absence of nucleic acids, such as microbial nucleic acids. The present invention is therefore useful in detecting viruses, bacteria and fungi, for example from a sample (such as a swab) obtained from a surface. The invention can also be used to test liquids, such as water supplies.

The human or animal patient, or sample obtained from the environment, can be tested for a variety of diseases and conditions using the invention, for example cancer, infection or genetic disorders.

Cancers include acute lymphoblastic leukemia, acute or chronic lymphocytic or granulocytic tumor, acute myeloid leukemia, acute promyelocytic leukemia, adenocarcinoma, adenoma, adrenal cancer, basal cell carcinoma, bone cancer, brain cancer, breast cancer, bronchi cancer, cervical dysplasia, chronic myelogenous leukemia, colon cancer, epidermoid carcinoma, Ewing's sarcoma, gallbladder cancer, gallstone tumor, giant cell tumor, glioblastoma multiforma, hairy-cell tumor, head cancer, hyperplasia, hyperplastic corneal nerve tumor, in situ carcinoma, intestinal ganglioneuroma, islet cell tumor, Kaposi's sarcoma, kidney cancer, larynx cancer, leiomyomater tumor, liver cancer, lung cancer, lymphomas, malignant carcinoid, malignant hypercalcemia, malignant melanomas, marfanoid habitus tumor, medullary carcinoma, metastatic skin carcinoma, mucosal neuromas, mycosis fungoide, myelodysplastic syndrome, myeloma, neck cancer, neural tissue cancer, neuroblastoma, osteogenic sarcoma, osteosarcoma, ovarian tumor, pancreas cancer, parathyroid cancer, pheochromocytoma, polycythemia vera, primary brain tumor, prostate cancer, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor.

Infections include bacterial, viral, fungal and parasitic infections. Bacterial infections include *Bacillus, bartonella, Bordetella, borrelia, Brucella, Campylobacter, Chlamydia, Chlamydophila, Clostridium, Corynebacterium, Enterococcus, Escherichia, Francisella, Haemophilus, Helicobacter,*

*Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio* and *Yersinia* infections. Viral infections include alphavirus, enterovirus, flavivirus, hepatitis A virus, hepatitis B virus, hepatitis C virus, hepatitis E virus, deltavirus, cytomegalovirus, herpes virus, lentivirus, dengue virus, Epstein-Barr virus, HIV, HPV, pneumovirus, influenza virus, arenavirus, norovirus, morbillivirus, cardiovirus, rubulavirus, rabies virus, rotavirus, rubella virus, Venezuelan equine encephalitis virus, western equine encephalitis virus, west nile virus, yellow fever virus and zika virus infections. Fungal infections include athlete's foot (*Tinea pedis*), nail infections (*Tinea unguium*), ringworm, intertrigo, *Pituriasis versicolor* (*Tinea versicolor*) infections and thrush (*Candida albicans*). Parasitic infections include *Entamoeba histoloitica, Giardia lamblia, Cryptosporidium parvum, Trichomonas vaginalis, Plasmodium malariae, Toxoplysma gondii, Pneumocystis jiroveci, Trypanosoma cruzi, Trypanosoma gambiense, Leishmania donovani, Diphyllobothrium latum, Echinococcus granulosus, Taenia saginata, Taenia solium, Schistosoma mansoni, Clonorchis sinensis, Paragonimus westermani, Ancylostoma duodenale, Ascaris lumbricoides, Enterobius vermicularis, Strogyloides stercoralis, Trichinella spi rallis, Trichuris trichiura, Dracunculus medineinsis, Loa loa, Onchocerca volvulus, Wuchereria bancrofti, Toxocara canis, Pediculus humanus, Dermetobia huminis, Sarcoetes scabiei, Dermacentor* and *Latrodectus mactans* infections.

Genetic disorders include 22q11.2 deletion syndrome, Angelman syndrome, Canavan disease, Charcot-Marie-Tooth disease, Cri du chat, cystic fibrosis, Down's syndrome, Duchenne muscular dystrophy, haemochromatosis, haemophilia, Klinefelter syndrome, neurofibromatosis, phenylketonuria, polycystic kidney disease, Prader-Willi syndrome, sickle-cell disease, spinal muscular atrophy, Tay-Sachs disease and Turner syndrome. Of particular relevance is Down's syndrome and other aneuploidies, as the present invention can be used to detect such diseases in a sample obtained from a pregnant female, in particular a blood sample comprising cell-free fetal DNA (non-invasive prenatal testing, NIPT).

There is therefore provided a method of testing for a disease, condition or organism, comprising:
   a. contacting a sample comprising a nucleic acid of interest with an extension adaptor or mixture of extension adaptors of the invention;
   b. ligating an extension adaptor to one or both ends of a nucleic acid of interest;
   c. extending the nucleic acid of interest over the ligated extension adaptor to generate a random tag on the nucleic acid of interest;
   d. amplifying the tagged nucleic acid of interest;
   e. determining the sequence and/or frequency of the nucleic acid of interest; and
   f. determining the presence of absence of the disease, condition or organism by comparing the sequence and/or frequency of the nucleic acid of interest with a reference.

The invention also provides a method for testing for a disease, condition or organism, comprising, the method comprising:
   a. providing a NAOI with random tag obtained by a method of tagging a NAOI of the invention;
   b. amplifying the tagged nucleic acid of interest;
   c. determining the sequence and/or frequency of the nucleic acid of interest; and
   d. determining the presence of absence of the disease, condition or organism by comparing the sequence and/or frequency of the nucleic acid of interest with a reference, e.g. a reference sequence or value.

The invention also provides a method for testing for a disease, condition or organism, comprising, the method comprising:
   a. providing an amplicon prepared by tagging and subsequent amplification of a NAOI according to a method of tagging of the invention as described herein;
   b. determining the sequence and/or frequency of the nucleic acid of interest; and
   c. determining the presence of absence of the disease, condition or organism by comparing the sequence and/or frequency of the nucleic acid of interest with a reference, e.g., a reference sequence or value.

The reference may be the sequence of a NAOI that is associated with the disease, condition or organism. The sample may be a patient sample or a sample obtained from the environment, for example the source of the sample is being tested for the presence of a particular organism.

Figure 1:
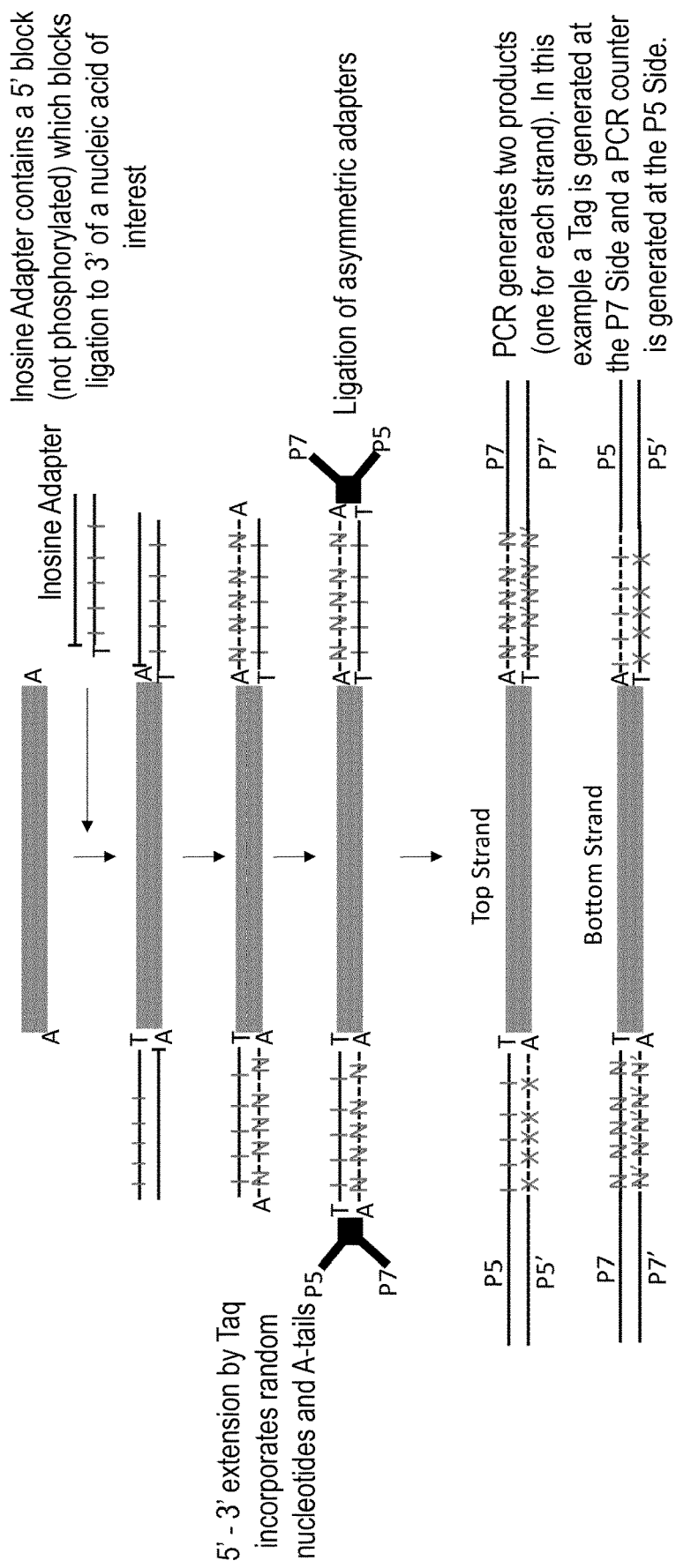
FIG. 1—A scheme for generating molecular tags by extension. A double-stranded (ds) adapter as shown has a first strand containing universal bases (inosines) hybridized to a second strand that contains a 5' block (non-phosphorylated) to prevent ligation of the strand containing the 5' block to a 3'-OH on a nucleic acid of interest; the 3-5' strand containing inosines has a 3' T overhang. A 5'-3' extension reaction by Taq polymerase incorporates nucleotides at random opposite inosines to generate a tag and A-tails. Asymmetric adapters are ligated to the tagged product. PCR is performed and generates two products (one for each strand of the originating, i.e., original, "parental" NAOI). In this example a Tag (of fixed sequence) is generated at the P7 Side and a PCR counter is generated at the P5 Side.
Figure 2:
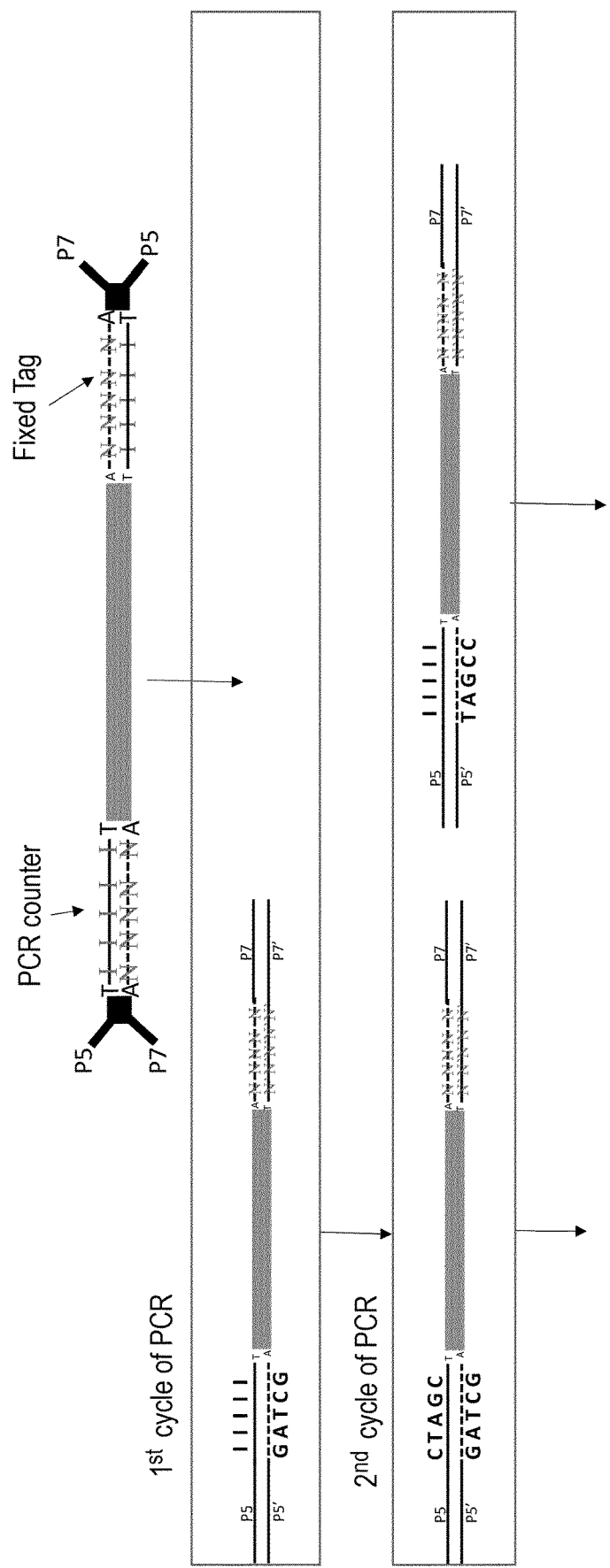
FIG. 2—A scheme for PCR amplification of a tagged and labelled NAOI
Figure 2:
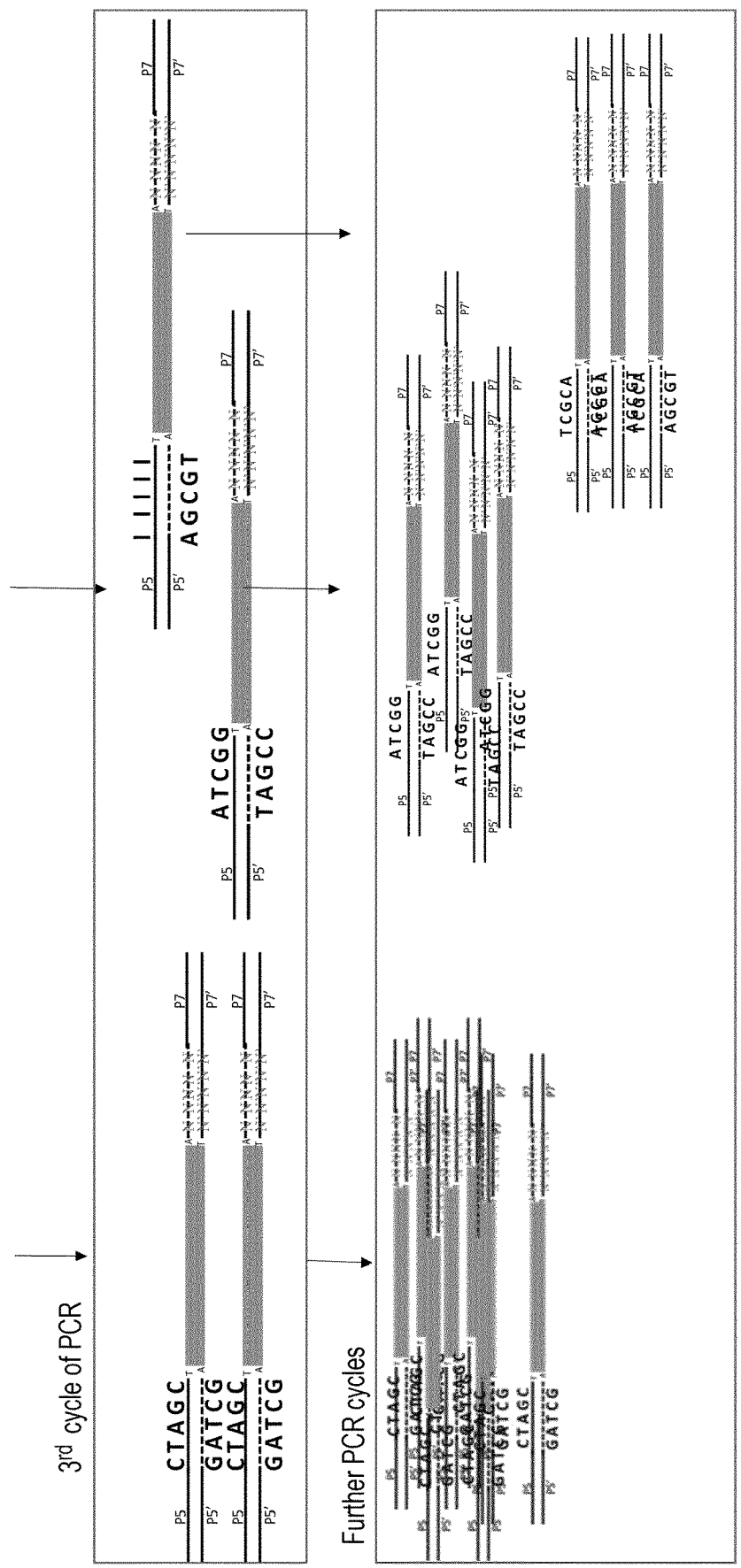

Referring now to FIG. 1, a nucleic acid of interest is end-repaired and A-tailed using methods common in the art (e.g., Kapa Hyper Prep™, NebNext™, Taq Based A-tailing). Ligation is performed using T4 DNA ligase and a double-stranded (ds) extension adaptor, the double-stranded extension adaptor comprises a first strand comprising universal bases (e.g., inosines) and has a 3' T-overhang and a second strand that is not phosphorylated at the 5' end. The second strand of the extension adaptor is phosphorylated at the 3' end to prevent ligation of adapters to one another (adapter dimerization).

A double-stranded adaptor is ligated to the nucleic acid of interest (at one or preferably both termini of the double-stranded nucleic acid of interest). The non-phosphorylated base at the 5' end of one strand of the adaptor prevents ligation of this adaptor strand to the 3' ends of the strands of the double stranded nucleic acid of interest, thus only the 3' end of the adaptor strand comprising one or more universal bases is ligated to the 5' end of the double-stranded nucleic acid of interest, adaptors may be ligated in this manner at one or each terminus of the NAOI. The strand of the adaptor that is ligated to the NAOI comprises a 3' T tail and one or more universal bases, preferably a series of universal bases (or a mix of universal and standard nucleotides), to serve as a template for generation of a unique tag by extension from the 3'OH of the complementary strand of the NAOI (extending over the ligated strand by using the ligated strand as a template for incorporation of bases into the strand being synthesised by extension). Bases are inserted at random opposite each universal base, thereby generating a plurality of unique tags from the same adaptor template. The adaptor could be a single-stranded adaptor (corresponding to the first strand of double stranded adaptor of the invention, i.e., comprising one or more universal nucleotide bases and a ligation moiety at its 3' end) although the efficiency of the reaction may be impacted.

A 5'-3' extension reaction using Taq polymerase leads to loss of the non-ligated adaptor strand and incorporates nucleotides randomly into the double-stranded NAOI by extension in a 5'-3' direction (using the ligated adaptor strand that comprises universal bases as a template) to generate unique tags. Taq polymerase adds an additional A overhang at the 3' end of the extended molecule, thereby providing an A-tail for ligation of asymmetric adaptors such as Y stem adaptors, e.g., Illumina™-compatible adaptors such as P5 and P7 adaptors. The product of these steps, a nucleic acid of interest to which unique barcodes have been added by extension and to which the asymmetric adaptors have been ligated, is used as a template for amplification, suitably by PCR.

Thus, following ligation of asymmetric adaptors to the double-stranded product of the extension step, a PCR reaction is performed. Each PCR reaction will generate two distinct products (amplicons), one from each strand of the double-stranded product of the previous labelling step. Only the barcode tag on one end of each amplicon (in FIG. 1, the ends derived from each P7 3' end of the double-stranded product of the labelling step) will be constant as the universal bases at each 5' end of the strand of the double-stranded product of the labelling steps (NAOI+UB adaptor+ Asymmetric adaptor) will generate a new barcode in each successive cycle of PCR. The new barcode generation could be used as a PCR counter, with every new PCR product generated from the parental strand generating a new barcode.

Further Methods of the Invention

The present invention also provides a method, comprising:
 a. obtaining a sample from a patient, said sample comprising a plurality NAOIs, optionally wherein the NAOIs are cell-free DNA (cfDNA) molecules; and
 b. determining the sequence of one or more of the NAOIs according to a method of the invention as described herein.

The methods of the invention may further comprise a step of determining the presence or absence of a NAOI in the sample, or the presence or absence of a genetic alteration (e.g., mutation or variant) in the nucleic acid of interest. The step of obtaining the sample may be a step of the method, or alternatively the method may be carried out using a sample previously obtained from a patient.

In further embodiments of the invention, the methods may comprise mapping the sequence reads to a reference genome.

Methods provided herein include a method of diagnosing cancer, a method of determining cancer prognosis, a method of determining cancer remission or relapse, a method of detecting progression of cancer, or a method of determining the presence or absence of residual cancer, wherein the cfDNA is circulating tumour DNA (ctDNA) and the method further comprises determining the presence or absence of a genetic alteration in the ctDNA. In such methods, the NAOI is contained within or derived from a patient sample. The sample is obtained from a patient that has, is suspected of having, or has had, cancer. The present invention therefore provides:

(I) A method of diagnosing cancer, comprising:
 a. providing a sample from a patient, said sample comprising a plurality of ctDNAs;
 b. determining the sequence of one or more of the ctDNAs according to a method of the invention as described herein;
 c. determining the presence or absence of one or more genetic alterations in the ctDNAs; and
 d. determining the presence or absence of cancer based on the presence or absence respectively of the one or more genetic alterations.

(II) A method of determining cancer remission or relapse, comprising:
 a. providing a sample from a patient, said sample comprising a plurality of ctDNAs;
 b. determining the sequence of one or more of the ctDNAs according to a method of the invention as described herein;
 c. determining the presence or absence of one or more genetic alterations in the ctDNAs; and
 d. determining cancer remission or relapse based on the absence (or decrease in frequency of) or presence respectively of the one or more genetic alterations.

(III) A method of detecting progression of cancer, comprising:
 a. providing a sample from a patient, said sample comprising a plurality ctDNAs;
 b. determining the sequence of one or more of the ctDNAs according to a method of the invention as described herein;
 c. determining the presence or absence of one or more genetic alterations in the ctDNAs, or determining a change in the abundance of the one or more genetic alterations;
 d. optionally comparing the results from step (c) to the results for the same patient using a sample obtained at a previous point in time; and
 d. determining a progression of cancer based on the presence or absence of the one or more genetic mutations, or based on a change in the abundance of the one of more genetic alterations.

(IV) A method of determining the presence of residual cancer, comprising:
 a. providing a sample from a patient, said sample comprising a plurality ctDNAs;
 b. determining the sequence of one or more of the ctDNAs according to a method of the invention as described herein;
 c. determining the presence or absence of one or more genetic alterations in the ctDNAs; and
 d. determining the presence of residual cancer based on the presence or absence of the one or more genetic alterations.

The above methods may be carried out on patients that are undergoing or have undergone cancer treatment. Alternatively, the above methods may be determinative in the treatment regimen for a cancer patient. For example, progression of cancer may be a worsening or improvement. If a worsening of cancer is detected, the patient may be treated with a different or more aggressive chemotherapy and/or radiotherapy. If a sufficient improvement is detected, treatment may be ended. To determine a progression of cancer, it may be possible to analyse only one sample from a patient. For example, a genetic alteration (such as a cancer mutation) may be detected that is indicative of late stage or aggressive cancer. Alternatively, the results may be compared with a sample obtained from the same patient at an early point in time. For example, the earlier sample may have been obtained from the same patient prior to onset or diagnosis of cancer. Alternatively, the earlier sample may have been obtained from the same patient prior to or at an earlier stage of treatment. In this way, the progression of cancer in a patient can be measured by carrying out an analysis on two or more samples obtained from a patient at different points in time.

There is therefore also provided a method of treating cancer, comprising treating a patient for cancer, wherein the patient has been determined as having cancer or at risk of a worsening of cancer or of cancer remission or relapse using a method of the invention.

In one embodiment, the method of treatment comprises:
a. providing a sample from a patient, said sample comprising a plurality ctDNAs;
b. determining the sequence of one or more of the ctDNAs according to a method of the invention as described herein;
c. determining the presence or absence of one or more genetic alterations in the ctDNAs;
d. selecting a cancer treatment regimen for the patient according to the presence or absence of a genetic alteration in the cell-free nucleic acid molecules; and
e. administering said cancer treatment regimen to the patient when one or more genetic alterations are detected.

Such a method may alternatively comprise:
a. determining the presence or absence of one or more genetic alterations in a library of sequence reads, the sequence reads having been obtained according to one of the methods of the invention described herein;
b. selecting a cancer treatment regimen for a patient according to the presence or absence of a genetic alteration in the cell-free nucleic acid molecules; and
c. administering said cancer treatment to the patient when one or more genetic alterations are detected.

The present invention also provides a method of determining a treatment regimen, such as a cancer treatment regimen, for a patient, for example a cancer patient or a patient suspected of having cancer, comprising:
a. providing a sample from a patient, said sample comprising one or more cell-free nucleic acid molecules
b. determining the sequence of one or more of the cell-free nucleic acid molecules according to a method of the invention as described herein;
c. determining the presence or absence of a genetic alteration in the cell-free nucleic acid molecules; and
d. selecting a treatment regimen for the patient according to the presence or absence of a genetic alteration in the cell-free nucleic acid molecules.

Such a method may alternatively comprise:
a. determining the presence or absence of one or more genetic alterations in a library of sequence reads, the sequence reads having been obtained according to one of the methods described herein; and
b. selecting a treatment regimen for the patient according to the presence or absence of a genetic alteration in the library of sequence reads.

In some embodiments, the methods include the step of administering treatment.

In embodiments relating to treatment of diseases (such as cancer) or selecting a treatment regimen for a disease (such as cancer), the treatment may be based on the results of the genetic analysis. In some embodiments, the presence of a genetic alteration may be indicative of disease, or indicative of resistance or susceptibility to certain treatments. In some embodiments, the frequency of a genetic alteration may be indicative of disease, or indicative of resistance or susceptibility to certain treatments. In such embodiments, the method may further comprise the step of comparing the results of the genetic analysis to a reference (such as a healthy control or a control taken from the same patient at a different point in time). The skilled person would be able to interpret the results of the genetic analysis, depending on the context. Additionally or alternatively, the methods may include conducting an analysis on two or more samples obtained from the same patient at different points in time. In this way, disease progress and the success or failure of treatments can be monitored.

The present invention also provides a method of predicting a patient's responsiveness to a cancer treatment, comprising
a. providing a sample from a patient, said sample comprising a plurality of cell-free DNA (cfDNA) molecules;
b. determining the sequence of one or more of the cfDNA molecules according to a method of the invention as described herein;
c. determining the presence or absence of a genetic alteration; and
d. predicting a patient's responsiveness to a cancer treatment according to the presence or absence of a genetic alteration.

Such a method may alternatively comprise:
a. determining the presence or absence of one or more genetic alterations in a library of sequence reads, the sequence reads having been obtained according to one of the methods described herein; and
b. predicting a patient's responsiveness to a cancer treatment according to the presence or absence of a genetic alteration in the library of sequence reads.

The treatment to be administered will generally be chemotherapy and/or radiotherapy. The specific treatment regimen may depend on the type of cancer that is detected. For example, some genetic alterations (e.g., mutations) may be indicative of a particular resistance or susceptibility to certain treatments, and the treatment regimen can be designed accordingly.

The genetic alterations being detected are not limited in the present invention and are known and understood by the skilled person. Indeed, methods of the present invention can be used to detect new or existing genetic alterations and associate those alterations with particular cancers or particular patient outcomes, for example susceptibility or resistance to particular treatment regimens.

Generally, the type genetic alteration or genetic variation being detected will depend on the context. For example, an alteration, variation or mutation that affects the amount or activity of the gene or gene product, as compared to the normal or wild-type gene. The alteration can be in amount, structure, and/or activity in a diseased tissue or cell (e.g., cancer tissue or cell), as compared to its amount, structure, and/or activity, in a normal or healthy tissue or cell (e.g., a control), and is associated with a disease state, such as cancer. Alternatively, the genetic alteration might be indicative of a genetic disease.

An alteration might have an altered nucleotide sequence (e.g., a mutation), amino acid sequence, chromosomal translocation, intra-chromosomal inversion, copy number, expression level, protein level, protein activity, or methylation status, in a cancer tissue or cancer cell, as compared to a normal, healthy tissue or cell. Exemplary alterations include, but are not limited to, point mutations (e.g., silent, missense, or nonsense), deletions, insertions, inversions, linking mutations, duplications, translocations, inter- and intra-chromosomal rearrangements. Mutations can be present in the coding or non-coding region of the gene. In certain embodiments, the alteration(s) is detected as a rearrangement, e.g., a genomic rearrangement comprising one or more introns or fragments thereof (e.g., one or more rearrangements in the 5'- and/or 3'-UTR). In certain embodiments, the alterations are associated (or not associated) with a phenotype, e.g., a cancerous phenotype (e.g., one or more of cancer risk, cancer progression, cancer treatment or resistance to cancer treatment). In one embodiment, the alteration is associated with one or more of: a genetic risk factor for cancer, a positive treatment response predictor, a negative treatment response predictor, a positive prognostic factor, a negative prognostic factor, or a diagnostic factor.

Alterations and mutations may be or may occur in or at: a single nucleotide position; an intragenic region or an intergenic region; an exon or an intron, or a fragment thereof; a coding region or a non-coding region; a promoter, an enhancer, a 5' untranslated region (5' UTR), or a 3' untranslated region (3' UTR), or a fragment thereof; a cDNA or a fragment thereof; an SNP; a somatic mutation, a germ line mutation or both; a point or a single mutation; a deletion mutation; an in-frame deletion, an intragenic deletion, a full gene deletion; an insertion mutation; an intragenic insertion; an inversion mutation; an intra-chromosomal inversion; a linking mutation; a linked insertion mutation; an inverted duplication mutation; a tandem duplication; an intrachromosomal tandem duplication; a translocation; a chromosomal translocation, a non-reciprocal translocation; a rearrangement; a genomic rearrangement; a rearrangement of one or more introns, or a fragment thereof; a rearranged intron; or a combination thereof.

In embodiments of the invention relating to cancer, the genetic alteration will be a genetic cancer alteration, such as a cancer mutation, which is associated with cancer, or predictive of responsiveness or non-responsiveness to anti-cancer therapeutics.

Cancer progression is associated with accumulation of genetic alterations in cells. Alterations in tumor suppressor genes and oncogenes accumulate during tumor progression and may correlate with the clinical aggressiveness of cancer. A number of genes have been also identified that play a role in inducing or suppressing metastasis.

In one embodiment, methods of the invention can be used to target patient-specific mutations. As per, for example, Forshew et al., "Noninvasive identification and monitoring of cancer mutations by targeted deep sequencing of plasma DNA", 2012, *Sci Transl Med.*, May 30; 4(136):136ra68, a tumour or plasma sample from a patient is sequenced, for example using a broad method such as whole genome, exome or cancer panel sequencing. A capture panel targeting patient-specific somatic mutations identified during this sequencing can then be generated. Optionally, this capture panel can be combined with a non-patient-specific panel. Importantly the capture panel can include both driver and passenger mutations. A driver mutation is causally implicated in oncogenesis. It has conferred growth advantage on the cancer cell and has been positively selected in the microenvironment of the tissue in which the cancer arises. A driver mutation need not be required for maintenance of the final cancer. A passenger mutation has not contributed to cancer development. Passenger mutations are found within cancer genomes because somatic mutations without functional consequences often occur during cell division. Thus, a cell that acquires a driver mutation will already have biologically inert somatic mutations within its genome. These will be carried along in the clonal expansion that follows and therefore will be present in all cells of the final cancer.

The capture panel can then be used with the methods of the invention described herein to diagnose, monitor or characterise a cancer in a patient. By screening for a large number of mutations previously identified in the patient there is an improved ability to detect cancer DNA and a more accurate ability to quantify average levels, since even if the tumour evolves it is unlikely that it will lose all mutations. Equally, even if less than 1 copy of the cancer genome is analysed by screening for multiple changes, detection is still possible using the methods of the invention as the error correction aspect provides methods with significantly increased accuracy over the prior art.

Accordingly, in a further aspect of the invention there is provided a method of monitoring disease progression of cancer in an individual, said method comprising
  (a) determining according to a method of the invention as described herein the presence or absence of one or more genetic alterations associated with a cancer in body fluid samples obtained from said individual at a plurality of time points following diagnosis of said individual with cancer;
  (b) comparing the results obtained at each time point in order to determine the progression of the cancer in said individual; wherein the same or an increase in genetic alteration levels between samples taken at different time points indicates an increase in cancer burden, and wherein a decrease in cancer alteration levels between samples taken at different time points indicates cancer regression.

In one embodiment, the step of determining the presence or absence of one or more genetic alterations associated with cancer is carried out after initiation of treatment.

In some embodiments, the results are further compared with genetic alteration levels determined prior to initiation of treatment from an initial or primary sample of fluid or tissue obtained from the individual following diagnosis with cancer. For example an initial genetic alteration profile may be established from a tumor tissue sample obtained from the individual and/or from a blood sample.

There is also provided a method of stratifying a microbial population, comprising:
  a. obtaining a sample comprising a plurality of microbial nucleic acids of interest;
  b. determining the sequence of one or more of the microbial nucleic acids of interest according to a method of the invention as described herein;
  c. mapping the sequence reads obtained in step b to a reference genome or genomes; and
  d. stratifying the microbial population according to the identified microbes.

Methods of Analysing Sequence Reads

The present invention is useful in identifying true genetic alterations (for example mutations) in a NAOI and distinguishing such alterations from "false" alterations introduced by the steps of the method, in particular during PCR and sequencing. The polymerases used in PCR are not 100% accurate. Indeed, when using a Taq polymerase, the error rate may be 1%. However, the present invention is useful in identifying these errors. The present invention is therefore also useful in determining the true sequence of a NAOI, such as determining the presence or absence of variations in a NAOI (such as a SNP).

In one embodiment, the invention provides a method of error correcting nucleic acid sequence reads, the method comprising:
  a. providing a dataset comprising a plurality of sequence reads from a sample, each sequence read comprising a PCR counter, the sequence of a nucleic acid of interest, and a tag;
  b. grouping sequence reads by tag or by tag and NAOI sequence similarity and aligning the sequence reads; and
  c. correcting errors in the sequence reads to provide a consensus sequence for each originating nucleic acid of interest.

In preferred aspects of all methods of the invention, sequences are grouped by tag and/or NAOI sequence similarity and aligned to generate a consensus sequence; sequences may be grouped by tag sequence similarity and aligned, or grouped by tag and NAOI sequence similarity and aligned, or grouped by NAOI sequence similarity and then by tag sequence similarity and aligned.

In preferred aspects, sequences are grouped by tag sequence and aligned, or grouped by tag sequence and NAOI sequence similarity and aligned. Tagging methods described herein will generally provide a unique tag for each NAOI, thus sequences with a common (identical) tag will almost certainly be progeny of a single parental (originating) NAOI from the original sample. Sequences with a common tag may also be grouped by NAOI sequence similarity. In the unlikely event that two dissimilar NAOI have a common (i.e., identical) tag, then the NAOI can be distinguished based on their dissimilar sequence.

To compare the NAOI sequences of the sequenced sample to each other and/or to a reference sequence, the sequences are aligned ("mapped") to each other and/or to a reference sequence; variation within the sequences can then be identified. Reads may be aligned to each other and/or to a reference sequence and analysed using bioinformatics software. Tools for mapping high-throughput sequencing data are reviewed by Fonseca et al., Bioinformatics. 2012 Dec. 15; 28(24):3169-77, the content of which are incorporated herein in its entirety.

After alignment, differences can be identified between the sequences and/or between the sequences and a reference sequence (e.g. a reference genome sequence). To identify variation, sequences are grouped by sequence similarity; the comparison allows some mismatches and small structural variation (InDels) in sequence. By consideration of the presence of a common tag on similar NAOI sequences and optionally combining information from the PCR counters, the sequence of the parental NAOI can be determined; errors introduced during processing can be identified and corrected to provide a consensus sequence for the NAOI. A scheme for this determination is shown in the Figures.

The sequence reads generated in methods of the invention will each have a PCR counter sequence, a sequence of the nucleic acid of interest, and a tag sequence. The sequence of the nucleic acid of interest will generally be disposed between the PCR counter and tag on each sequence read. Therefore, in some embodiments, each sequence read comprises, in a 5' to 3' or 3' to 5' order, a PCR counter, the sequence of a nucleic acid of interest, and a tag.

Depending on the length of the sequence reads in the initial sequence run, it might be the case that not every initial sequence read includes the entirety of the PCR counter, the sequence of the nucleic acid of interest, and the tag. For example, if the number of nucleotides making up the PCR counter, the sequence of the nucleic acid of interest and the tag is, for example, 200 nucleotides, but the first round of sequencing (determining the sequence of the forward strand) only sequences the first 150 base pairs, then not all of the sequences might be present in the initial sequence read. It may therefore be necessary to additionally sequence the reverse stand and, usually using a computer program, determining the complete sequence for the forward strand such that the final sequence read comprises the entire PCR counter, sequence of the nucleic acid of interest, and tag. Such methods are standard in the art. Hence references herein to sequence reads and libraries for analysis and/or error correction refer to the entire sequence (PCR counter, NAOI, and tag), and the skilled person would understand what steps are necessary to ensure the entire sequence is provided (for example, as determined by the length of the molecule being sequenced and the number of residues sequenced in each sequence run).

In some embodiments of the invention, the sequence reads further comprise one or more index sequences that act as sample identifiers. For any given sequence read, the index sequence(s) is/are different to the sequence of the PCR counter, the nucleic acid of interest, and the tag. When two or more index sequences are present, the index sequences are generally different from each other. In some embodiments, all sequences originating from the same sample will share at least one common index sequence. The index sequences may have been introduced at any stage, for example as part of the original extension adaptor or as part of a sequencing adaptor. Alternatively, they could have been separately ligated on to the NAOI.

If the design of the extension adaptors or mixture of extension adaptors is sufficiently complex, then all sequence reads having the same tag are from the same originating nucleic acid of interest. However, it is theoretically possible (albeit remotely) that the same tag sequence could be generated (at random) for more than one originating NAOI. Therefore, grouping/alignment of the sequences may be achieved using both the tag sequence and the sequence of the NAOI.

In some embodiments of the invention, methods comprising determining the sequence of one or more NAOIs or cfDNA molecules comprises a step of determining a consensus sequence for the NAOI of cfDNA molecule(s). This may comprise grouping or aligning all sequence reads having the same tag and obtaining a consensus sequence for that nucleic acid of interest. The sequence of the NAOI itself can also be used to help group the sequence reads according to individual starting molecules. For example, although the extension adaptors are designed to have sufficient complexity that a large number of different barcode tags are generated by the extension reaction, the possibility of the same tag being generated on two different starting NAOIs cannot be completely eliminated. However, the sequence of the NAOI itself can distinguish between two different starting NAOIs that have the same barcode tag.

A consensus sequence can be defined as a sequence occurring in at least 20%, at least 30%, at least 40% 50%, at least 60%, at least 70%, at least 80% or at least 90% of all sequence reads for a single originating nucleic acid of interest. Preferably the sequence occurs in at least 50% of the sequence reads. In this way, the method can be used to determine the true sequence of a starting molecule and to reduce or eliminate errors introduced by the method, in particular errors introduced by the polymerase in PCR reactions. The present invention is advantageous as no errors can be introduced at the stage of tagging the NAOI, since the tag is generated randomly and regardless of what sequence is generated by the polymerase at that stage, the resulting sequence will be the sequence of the tag.

The PCR counter is an indicator of the number of times a given sequence is amplified from an originating nucleic acid of interest. In some embodiments of the invention, the method may comprise determining the number of PCR counters for each group of sequence reads. A consensus sequence may then be obtained by retaining the sequence having the highest number of different PCR counters as a consensus sequence for the originating nucleic acid of interest.

Often, identification of the consensus sequence may be done by reference to a combination of the number of reads and the number of PCR counters. For example, if a consensus sequence cannot be determined solely by the number of reads originating from a parental NAOI (for example, no sequence accounts for more than 50% of sequence reads), then reference can be made to the number of PCR counters for each read to help reach a decision on the consensus sequence. In one embodiment of the invention, the step of determining a consensus sequence requires determining the frequency with which a given sequence is present in the dataset of sequence reads and determining the number of different PCR counters associated with that sequence. A determination of the consensus sequence can then be made accordingly.

In one embodiment of the invention, the dataset is obtained by conducting next generation sequencing on a mixture of tagged originating nucleic acids of interest. The dataset may be obtained using a method of tagging a NAOI or a method of determining the sequence of a NAOI as described herein.

In some embodiments, each originating nucleic acid of interest has a unique tag. However, it may be the case that more than one originating NAOI molecule has the same tag. In such cases, the sequence of the NAOI itself and the sequence of the extension tag can be used to uniquely identify the originating molecule.

For example, a genome may be approximately 3,000,000,000 bp long. If it is fragmented into 160 bp fragments, a single copy of the haploid genome would make ~18,750,000 fragments. If the analysis included, for example, 1000 copies of the genome, this would provide 18,750,000,000 fragments. A single tag sequence having 12 universal bases will provide up to 16,777,216 unique tags. Therefore, for complex analyses in which there are a large number of fragments, it will be necessary for the sequence reads to be grouped such that all sequence having the same tag and the same or similar NAOI sequence are grouped together to identify unique originating NAOIs.

It is also possible that the sequence of different NAOI fragments from the same sample will be overlapping. Hence, grouping or alignment may occur with reference to the tag sequence and one or more contiguous residues of the NAOI (preferably at least 10 residues of the NAOI, such that all reads having the same tag and having at least 10 contiguous overlapping residues in the NAOI are grouped).

The method may additionally comprise a step of mapping the sequence reads to a reference genome. Generally the reference genome will be from the same species from which the NAOI originated. The step of mapping of the sequence reads to a reference genome may occur prior to grouping or aligning all sequence reads having the same tag. In some embodiments, the mapping of the sequence reads to a reference genome may occur after obtaining a consensus sequence.

The present invention also provides a method of counting sequencing reads comprising:
a. providing a dataset comprising a plurality of sequence reads from a sample, each sequence read comprising a PCR counter, the sequence of a nucleic acid of interest, and a tag,
b. grouping sequence reads by tag or by tag and NAOI sequence similarity and aligning to provide a consensus sequence for each originating nucleic acid of interest; and
c. counting the number of starting molecules to determine the copy number of the original NAOI.

The copy number of the original (originating) NAOI is the frequency with which a starting NAOI molecule occurred in the original sample. Therefore, in addition to cancer alterations resulting in changes in copy number, such methods may be useful in determining aneuploidy, such as fetal aneuploidy, using a sample obtained from a patient. Fetal aneuploidy can be determined using cell-free fetal DNA obtained from a maternal sample, in particular a maternal blood or plasma sample. The present invention therefore also provides method of determining the present of absence of aneuploidy, such as fetal aneuploidy, using methods described herein.

The present invention also provides a method of distinguishing between a genetic alteration, variation or mutation in a nucleic acid of interest and an error introduced during processing of said NAOI, the method comprising:
a. providing a dataset comprising a plurality of sequence reads from a sample, each sequence read comprising a PCR counter, the sequence of a nucleic acid of interest, and a tag, wherein all sequence reads having the same tag are from the same originating nucleic acid of interest;
b. grouping sequence reads by tag or by tag and NAOI sequence similarity and aligning the sequence reads; and
c. correcting errors in the sequence reads to provide a consensus sequence for each originating nucleic acid of interest, thereby distinguishing between a genetic alteration, variation or mutation in a nucleic acid of interest and an error introduced by processing.

In some embodiments, step c) may comprise determining the number of different PCR counters associated with each NAOI and determining the consensus (i.e. true) sequence of the NAOI by keeping the sequence of the NAOI that is associated with the largest number of different PCR counters.

The present invention further provides a mixture or composition comprising a plurality of adaptors of the invention (i.e. a pool of adaptors) and one or more nucleic acids of interest. The one or more nucleic acids of interest may comprise a 3' ligation moiety that is complementary to the 3' ligation moiety on the adaptor. In some embodiments, the adaptors are ligated to the nucleic acids of interest. The nucleic acids of interest may be from 25 to 100,000 base pairs in length, from 25 to 50,000 base pairs in length, from 25 to 10,000 base pairs in length, from 25 to 1000 base pairs in length, from 50 to 500 base pairs in length in length, from 100 to 250 base pairs in length, or from 100 to 200 base pairs in length. In some embodiments, the nucleic acids of interest are double-stranded, for example double-stranded cfDNA obtained from a patient. The cfDNA may be ctDNA.

The invention also provides kits. The kit of parts comprises extension adaptors of the invention and instructions for use. The kit may also comprise one or more nucleotides in solution, for example, A, T, C and G nucleotides in solution. The adaptors and nucleotides in solution are disposed in separate containers. In some embodiments, the different types of nucleotides are disposed in separate containers.

In some embodiments of the invention, the kit further comprises enzymatic means for ligation or nucleic acids. The enzymatic means for ligation of nucleic acids can be a ligase, or example a DNA ligase, such as T4 DNA ligase. The kit may also (or alternatively) comprise enzymatic means for polymerisation of nucleic acids. The enzymatic means for polymerisation of nucleic acids can be a polymerase, such as a DNA polymerase, for example Taq DNA polymerase.

In some embodiments of the invention, each component of the kit is disposed in separate container, with one container comprising the pool of extension adaptors and optionally the nucleotides in solution (or the nucleotides in solution may be in a container or containers separate to the pool of extension adaptors).

In one embodiment of the invention, there is provided a method of tagging a double-stranded nucleic acid, comprising:
a. contacting the double-stranded nucleic acid with a mixture of double-stranded adaptors, each double-stranded adaptor comprising two strands, wherein the first strand comprises at least 4 universal nucleotide bases and a ligation moiety at its 3' end, and wherein the second strand comprises a ligation block at its 5' end;
b. ligating an adaptor to the 5' end of one or both strands of the double-stranded nucleic acid;
c. extending the nucleic acid of interest over the ligated adaptor in a 5' to 3' direction to provide a tagged double-stranded nucleic acid; and
d. preferably differentially labelling each strand of the tagged double-stranded nucleic acid by ligating asymmetric adaptors to each end of the tagged double-stranded nucleic acid to generate a tagged and labelled double-stranded nucleic acid.

When the tagged and labelled nucleic acid is to be sequenced, the method further comprises
e. removing un-ligated adaptors;
f. amplifying the tagged and labelled double-stranded nucleic acid; and
g. determining the sequence of the nucleic acid of interest.

Preferred features for the second and subsequent aspect of the invention are as provided for the first aspect of the invention, mutatis mutandis.

The invention will now be further illustrated by reference to specific examples, which are provided for reference and are not to be construed as limiting on the scope of the claims.

EXAMPLES

Example 1—Extension Adaptor Design

NextSeq Systems use 2-channel sequencing, which requires only 2 images to encode the data for 4 DNA bases: 1 red channel and 1 green channel. The NextSeq also uses a new implementation of Real-Time Analysis (RTA) called RTA2.0, which includes important architecture differences from RTA on other Illumina sequencing systems. For any index sequences, RTA2.0 requires that there is at least one base other than G in the 1st 2 cycles.

The HiSeq and MiSeq Systems use a green laser to sequence G/T and a red laser to sequence A/C. At each cycle at least 1 of 2 nucleotides for each colour channel must be read to ensure proper registration.

The important factors for extension adaptor design include:
ability to form a stable double-stranded structure
the presence of a suitable number of Universal Bases to generate a barcode tag,
sufficient complexity during the initial cycles of sequencing so that phasing calculations can be determined; and/or
adaptors suitable for high-efficiency ligation An example design for a full-length extension adaptor having 4 inosine residues is as follows (from top to bottom SEQ ID NOs:1-2):

```
5' GCACCCTCACCTCAGCATCTGACTC-P 3'
   |||||||||||||||||||||||||
3' T*CGTGIAGTGIAGICGIAGACTGAG-P 5'
```

Note that the inosine containing strand has a 5' phosphate group to allow ligation to the Y shaped Illumina adapter. Furthermore, the complementary strand is 3' phosphorylated to prevent blunt-ended ligation to a second adapter (adapter dimerization).

An alternative example, having 8 inosine residues is:

```
5-IGIAITICIAIGIAICGGAGT-3              (SEQ ID NO: 3)
  |||||||||||||||||||||
3-CCCTAACGCTACCTAGCCTC (C3-spacer)-    (SEQ ID NO: 4)
 5
```

Inosine has optimal pairing according to the order C>A>T>G, so C and A were selected to pair with the inosines.

Example 2—Asymmetric Adaptor Design

The invention can use asymmetric Y-stem adaptors, for example P7/P5 Illumina™-compatible adaptors:

```
5-ACACTCTTTCCCTACACGACGCTCTTCCGATCT-3   (SEQ ID
                   ||||||||||||        NO: 5)
  3-CTGACCTCAAGTCTGCACACGAGAAGGCTAGP-5  (SEQ ID
                                        NO: 6)
```

Underlined residues represent the asymmetric (non-complementary) portion of the Y-stem adaptor. The P is a 5' phosphorylation.

Example 3—PCR Primers for Amplification

Any suitable primer can be used, although examples are provided below, in particular for use in conjunction with the Y-stem adaptor exemplified above:

```
>i5 PCR primer (SEQ ID NO: 7)
5-AATGATACGGCGACCACCGAGATCTACAC[i5]

ACACTCTTTCCCTACACGACGCTCTTCCGATCT-3

>i7 PCR primer (SEQ ID NO: 8)
5-CAAGCAGAAGACGGCATACGAGAT[i7]

GTGACTGGAGTTCAGACGTGTGCTCTTCCGATCT-3
``` i5 and i7 are 8 bp sample identifiers (index sequences). The underlined residues represent the sections of the primers that are complementary to the corresponding asymmetric (non-complementary) portion of the Y-stem adaptor. The remaining residues at the 3' end of the two primers are complementary to the symmetrical (i.e. complementary) portion of the Y-stem adaptor.

Example 4—Reducing Risk of Phasing Issues Using a Mixture of Adaptors

The above design may have Illumina phasing issues, since when a sequencer reads the same base in all molecules at the same time it cannot determine clusters and therefore sequencing quality and yield could be reduced. To stop this from happening a mix of 4 types of adaptor could be used.

An example of a suitable mixture or pool of adaptors is provided below:

```
5-IACGIGIIGICGIICIAIAGIAGT-3       (SEQ ID NO: 9)
  |||||||||||||||||||||||
3-CTGCCCAACCGCAAGCTATCCTC          (SEQ ID NO: 10)
(C3-spacer)-5

5-GIAIGIAITIGIAIAIAICIGAGT-3       (SEQ ID NO: 11)
  ||||||||||||||||||||||||
3-CATCCCTAACCCTATCTAGCCTC          (SEQ ID NO: 12)
(C3-spacer)-5

5-CGCIGIIGIICIAIGIGICGGIGT-3       (SEQ ID NO: 13)
  ||||||||||||||||||||||||
3-GCGCCCACACGCTACCCAGCCAC          (SEQ ID NO: 14)
(C3-spacer)-5

5-AAIGIGAIAICIITIGIICGGAIT-3       (SEQ ID NO: 15)
  ||||||||||||||||||||||||
3-TTCCCCTATCGCCACCAAGCCTC          (SEQ ID NO: 16)
(C3-spacer)-5
```

A further example of a suitable mixture of adaptors is provided below (from top to bottom SEQ ID NOs:1, 2, 17-22):

```
5' GCACCTCACCTCAGCATCTGACTC-P 3'
   ||||||||||||||||||||||||
3' T*CGTGIAGTGIAGICGIAGACTGAG-P 5'

5' GCACCTCACCTCAGCATCGACTGAG-P 3'
   ||||||||||||||||||||||||
3' T*CGTGIAGTGIAGICGIAGCTGACTC-P 5'

5' GCACCTCACCTCAGCATCTACAGTCT-P 3'
   ||||||||||||||||||||||||||
3' T*CGTGIAGTGIAGICGIAGATGTCAGA-P 5'

5' GCACCTCACCTCAGCATCAATGTCAGA-P
   ||||||||||||||||||||||||||
3' T*CGTGIAGTGIAGICGIAGTTACAGTCT-P 5'
```

Note that the inosine containing strand has a 5' phosphate group to allow ligation to a Y shaped Illumina adapter. Furthermore, the complementary strand is 3' phosphorylated to prevent blunt-ended ligation to a second adapter (adapter dimerization). The asterisk represents a phosphothioate linkage between bases (as opposed to phosphodiester). A phosphothioate bond stops the adapter being digested by enzymes that have exonuclease activity.

Example 5—Tagging a Nucleic Acid of Interest

Standard library preparation (using Taq for A-Tailing) is performed using an adaptor containing universal bases. The adaptor contains a 3' block (unphosphorylated 5' nucleoside) on one strand and a 3' T-tail plus a series of universal bases in the other strand. The extension adaptor is ligated onto the target DNA of interest (FIG. 1). This generates a single-stranded ligation event. The adaptor comprises universal bases (e.g., inosines). Taq polymerase then extends in the 5' to 3' direction and inserts nucleotides randomly opposite the universal bases finishing with a 3' A-tail. Standard Y-Stem adaptors are added and ligated onto the extended double-stranded product. The bases generated by the extension reaction are used as a barcode tag. The inosines on the complementary strand will be "over-written" during every cycle of PCR. However, they can be used as a PCR counter, since a new counter will be generated for each cycle of PCR.

Standard Taq-based library preparation methods known in the art may be adapted for use in methods of the invention.

After the first ligation step, the temperature of the reaction mixture can be raised to 65° C., to inactivate the ligase and re-activate the Taq polymerase. Taq polymerase will extend over the inosines and will also A-tail. Taq makes DNA products that have A (adenine) overhangs at their 3' ends, this facilitates ligation of adaptors with a T (thymine) 3' overhang that complements the A-overhang product of the extension reaction, thus enabling efficient ligation of the extension product and Y-Stem adaptor.

The reaction temperature can be lowered (or a purification performed) and ligase and asymmetric (e.g. Y-Stem) adaptors can be added. Using this method, no additional purification steps are necessary and thus there is no loss of efficiency compared to standard protocols. The first ligation event does not need to occur for all molecules present in the reaction mix, thus does not impact upon the efficiency of the labelling process.

Extension adaptors from the $1^{st}$ ligation may compete for ligation with the Y-stem adaptors in the $2^{nd}$ ligation step. Should this situation arise, it may be overcome using one or more of the following methods: 1) removing the extension adaptors using purification methods known in the art (preferably Ampure XP) 2) Having a high excess of Y-Stem adaptor present, so that the Y-adaptors out compete the extension adaptor for ligation 3) G-Tailing the NAOI and using C-Tailed extension adaptors (during the first ligation), then A-Tailing and using T-Tailed Y-stem adaptors. 4) Using single-stranded extension adaptors and treating with exonuclease to remove the single-stranded adaptors after the first ligation and extension. 5) Incorporating a RNA or Uracil nucleotide into the extension adaptor and removing the un-ligated adaptor after extension.

After tagging and labelling, the NAOIs are target enriched using an array (NimbleGen™ array capture enrichment). The enriched NAOIs are amplified using PCR and are ready for sequencing.

Example 5—Illumina Sequencing

Although any NGS sequencing method can be used, the following is an example of Illumina sequencing by synthesis involving bridge amplification.

The tagged, labelled and optionally enriched NAOIs are melted to provide single-stranded NAOIs and are bound randomly to the inside surface of flow cell channels. Unlabelled nucleotides and enzymes are added to initiate solid phase bridge amplification. The above step results in NAOIs becoming double stranded and bound to the substrate. The double stranded bridge is denatured to create to immobilized single-stranded genomic DNA (e.g., ssDNA) sequences complementary to one another. The above bridge amplification and denaturation steps are repeated multiple times to generate several million dense clusters of dsDNA (or immobilized ssDNA pairs complementary to one another) in each channel of the flow cell.

The reverse strands are removed but the 3' ends of the sequence are blocked to prevent hybridisation to the flow cell. The first sequencing cycle is initiated by adding a sequencing primer, all four labelled reversible terminators, primers, and DNA polymerase enzyme to the flow cell. The sequencing-by-synthesis (SBS) method utilizes four fluorescently labelled modified nucleotides having a reversible termination property, allowing each cycle of the sequencing reaction to occur simultaneously in the presence of all four nucleotides (A, C, T, G). In the presence of all four nucleotides, the polymerase selects the correct base to incorporate. All unincorporated labelled terminators are then washed off. Laser is applied to the flow cell. Laser excitation captures an image of emitted fluorescence from each cluster on the flow cell. A computer program records the identity of the first base for each cluster. Before initiating the next sequencing step, the 3' terminus and the fluorescence from each incorporated base are removed.

Subsequently, a second sequencing cycle is initiated by adding all four labelled reversible terminators, primers, and DNA polymerase enzyme to the flow cell. A second sequencing read occurs by applying a laser to the flow cell to capture emitted fluorescence from each cluster on the flow cell which is read and analysed by a computer program. The sequencing steps are repeated 150 times to sequence the NAOI. After 150 cycles, the read product is washed away. A primer specific for the index sequence is added to initiate sequencing of the index sequence, achieved in the same manner as described above. The index read is washed away and the 3' ends of the remaining immobilised strand unblocked to enable priming of both ends to the flow cell. A second primer for a second index sequence is added, followed by sequencing of that second index sequence in the same manner. The second index read product is washed away and a polymerase used to complete bridge amplification. The resulting double stranded DNA is denatured and the 3' ends are blocked. The forward strand is removed and sequencing of the remaining reverse strand of the NAOI is conducted by repeating the sequencing cycle a further 150 times as set out above. In this way the entire NAOI, including the tag and the PCR counter, is sequenced. A computer program is used to align the reads and conduct further analysis.

Example 6—Error Correction of Sequencing Reads

A dataset comprising multiple sequence reads for each NAOI is generated as described above. Each paired end sequence read comprises a PCR counter, the sequence of a nucleic acid of interest, and a tag. The sequence reads are grouped and aligned according to the tag sequence and the sequence of the NAOI to provide sequence read groups, for example as set out in FIG. 3. Each member of a group of sequence reads originates from the same starting molecule.

Sequence reads having the same tag sequence are compared. Where all sequences of the NAOI sequence are the same, the sequence is used as a true representation of the original sequence of the NAOI. Where not all of the sequences of the NAOI sequence are identical across the groups, a consensus sequence is determined.

Where 70% or more of reads have the same NAOI sequence, this is taken as the consensus sequence for that NAOI and the other sequences are discarded as errors, as shown in the bottom half of the middle panel of FIG. 3.

Where less than 70% of reads have the same sequence, the number of PCR counters for each sequence read is determined. The sequence read having the largest number of different PCR counter sequences is retained as the consensus sequence and the remaining sequences are discarded as errors, as shown in the top half of the middle panel of FIG. 3.

An alternative schematic is provided in FIG. 4. The "X" represents an error in the sequence generated during PCR. In this example, an error is introduced in the $1^{st}$ and $5^{th}$ cycles of PCR. However, when the amplicons are grouped according to their tag sequence and NAOI sequence, the true sequence of the NAOI has the highest number of PCR counters and is retained as the consensus sequence.

Example 7—Detecting Cancer Relapse in a Patient

A blood plasma sample is obtained from a patient that has undergone treatment for cancer. ctDNA is extracted using a Qiagen extraction column. The DNA is end-repaired using a T4 DNA polymerase, phosphorylated, and A-tailed using a Taq DNA polymerase.

Extension adaptors are ligated onto the nucleic acid of interest. Purification using magnetic SPRI beads is undertaken to remove unligated extension adaptors. The adaptors are extended using Taq Polymerase to generate a barcode and an A-tail.

Asymmetric adaptors are ligated on to both ends of the tagged NAOIs, followed by purification using magnetic SPRI beads to remove excess unligated asymmetric adaptors. PCR amplification is then undertaken using PCR primers directed against the asymmetric portions of the asymmetric adaptors. The primers comprise a sample identifier that is unique to the patient's sample.

Target enrichment is undertaken using hybridisation based methods (Agilent SureSelect) to select for regions known to be susceptible to alteration or mutation in cancer. Further PCR amplification is then undertaken on the enriched sample.

The enriched and amplified NAOIs are sequencing using Illumina NGS and error correction is undertaken as described above.

The presence of a cancer mutation or alteration, or increase in prevalence of a cancer mutation or alteration, is indicative of cancer relapse and the patient may be recommended for treatment. The absence of a cancer mutation or alteration, or decrease in prevalence of a cancer mutation or alteration, is indicative of cancer remission. The patient may be discharged with a recommendation to undergo further screening in a year's time.

Example 8

Extracted DNA is blunted and A-tailed in 1× rapid T4 DNA ligase buffer containing 2 mM of each dNTP, 0.025 units/µL T4 DNA polymerase, 0.125 units/µL polynucleotide kinase and 0.0042 units/µL Taq DNA polymerase in a final reaction volume of 60 µl. Samples are incubated for 30 minutes at 20° C. followed by 30 minutes at 65° C. Barcoding adapters are ligated using 1 pmol/µl adapters and 20 units/µL T4 DNA ligase in a final reaction volume of 100 µl made up to this volume using 2× rapid T4 DNA ligase buffer and water. Samples are incubated at 20° C. for 30 minutes followed by 68° C. for 30 minutes. SPRI bead clean-up is performed following the manufacturers recommendations (Beckman Coulter). DNA is eluted in 17 µL Tris-HCl. Illumina adapters are ligated in 1× Blunt/TA Ligase Master Mix (NEB) using 1 pmol/µl adapters in a final reaction volume of 32 µL. Samples are incubated at 25° C. for 15 minutes. SPRI bead clean-up performed following the manufacturers recommendations (Beckman Coulter). DNA is eluted in 17 µL Tris-HCl. PCR amplification is performed using platinum SuperFi 2× Master Mix, with each PCR primer at a final concentration of 1 µM in a final reaction volume of 50 µL and with the following cycling parameters: 98° C. for 30 seconds, followed by 7 cycles of 98° C. for 10 seconds, 62° C. for 30 seconds and 72° C. for 1 minute; followed by a single final extension at 72° C. for 5 minutes and a final hold at 4° C. SPRI bead clean-up is performed following the manufacturers recommendations (Beckman Coulter). DNA is eluted in 17 µL Tris-HCl. DNA is quantified using KAPA Library Quantification Kit, following the manufacturer's instructions (KAPABIOSYSTEMS) and is sequenced on the NextSeq 500 Illumina platform following manufacturers recommendations (Illumina).

Example 9

Extracted DNA is blunted and A-tailed in a 1× rapid T4 DNA ligase buffer containing 2 mM of each dNTP, 0.025 units/μL T4 DNA polymerase, 0.125 units/μL polynucleotide kinase and 0.0042 units/μL Taq DNA polymerase in a final reaction volume of 60 μL. Samples are incubated for 30 minutes at 20° C. and for 30 minutes at 65° C. Barcoding adapters are ligated using 1 pmol/μL adapters and 20 units/μL T4 DNA ligase in a final reaction volume of 100 μL made up to this volume using 2× rapid T4 DNA ligase buffer and water. Samples are incubated at 20° C. for 30 minutes. SPRI bead clean-up is performed following the manufacturers recommendations (Beckman Coulter). DNA is eluted in 17 μL Tris-HCl. The molecular barcode is extended in 1× rapid T4 DNA ligase buffer using 0.0042 units/μL Taq DNA polymerase in the presence of dNTPs (dATP, dGTP and dTTP are each added to a final concentration of 2 mM and dCTP to a final concentration of 0.2 mM) in a final reaction volume of 60 μL. Samples are incubated at 65° C. for 30 minutes. Illumina adapters are added to the reaction to a final concentration of 1 pmol/μL, T4 DNA ligase is added to 20 units/μL and the reaction is made up to a final volume of 100 μL using 2× rapid T4 DNA ligase buffer and water. Samples are incubated at 20° C. for 30 minutes. SPRI bead clean-up is performed following the manufacturers recommendations (Beckman Coulter). DNA is eluted in 17 μL Tris-HCl. PCR amplification is performed using 0.02 units/μL Phusion U DNA Polymerase (ThermoFisher), 5× Phusion HF Buffer, dNTPS at a final concentration of 200 μM and each PCR primer at 1 μM final concentration in a final reaction volume of 50 μL and with the following cycling conditions: initial denaturation at 98° C. for 30 seconds followed by 7 cycles of 98° C. for 10 seconds, 62° C. for 30 seconds and 72° C. for 60 seconds, followed by a single final extension of 72° C. for 10 minutes and an infinite hold at 4° C. The concentrations of the individual dNTPs can me adjusted to favour/restrict the incorporation of certain bases opposite the universal base(s). SPRI bead clean-up is performed following the manufacturers recommendations (Beckman Coulter). DNA is eluted in 17 Tris-HCl. DNA is quantified using KAPA Library Quantification Kit, following the manufacturer's instructions (KAPABIOSYSTEMS) and is sequenced on the NextSeq 500 Illumina platform following manufacturers recommendations (Illumina).

The invention claimed is:

1. A double-stranded nucleic acid adaptor comprising a first strand and a second strand, wherein:
the 3' end of first strand overhangs the second strand;
the overhanging 3' end of the first strand is ligatable and comprises one or more non-universal bases;
the first strand has one or more universal nucleotide bases in the double-stranded region of the adaptor; and
the second strand has a ligation block at its 5' end.

2. The double-stranded nucleic acid adaptor of claim 1, wherein said non-universal bases are selected from the group consisting of A, T, C, G and U (Uracil).

3. The double-stranded nucleic acid adaptor of claim 1, wherein the overhanging 3' end of the first strand is a C or T overhang.

4. The double-stranded nucleic acid adaptor of claim 1, wherein the universal base is selected from the group consisting of 2'-deoxyinosine (inosine) and derivatives thereof, nitroazole analogues and derivatives thereof, hydrophobic aromatic non-hydrogen-bonding bases and derivatives thereof, 3'-nitropyrrole bases and derivatives thereof (for example 3'-nitropyrrole CE phosphoramidite), nitroindole bases and derivatives thereof (for example 4-, 5- and 6-nitroindole CE phosphoramidite and 5-nitroindole-3-carboxamide), 2'-deoxynucleoside and derivatives thereof, K-2'-deoxyribose, P-2'-deoxyribose, 2'-deoxyisoguanine and 2'-deoxynebularine.

5. The double-stranded nucleic acid adaptor of claim 1, wherein the universal base is inosine.

6. The double-stranded nucleic acid adaptor of claim 1, wherein the 5' ligation block on the second strand is selected from the group consisting of a non-phosphorylated nucleotide, an inverted dT, and a C3 spacer.

7. The double-stranded nucleic acid adaptor of claim 6, wherein the 5' ligation block is a non-phosphorylated nucleotide.

8. The double-stranded nucleic acid adaptor of claim 1, wherein the first and last base pairs of the double-stranded region of the adaptor do not comprise any universal bases.

9. The double-stranded nucleic acid adaptor of claim 1, wherein the first strand comprises at least 2 universal bases.

10. The double-stranded nucleic acid adaptor of claim 1, wherein the first strand comprises from 1 to 20 universal bases.

11. The double-stranded nucleic acid adaptor of claim 1, wherein the first stand comprises the following sequence, in a 5' to 3' order:

[X1]-[X2]-[X3]-[ligation moiety]

wherein:
X1=one or more non-universal bases;
X2=one or more universal bases, optionally further comprising one or more non-universal bases; and
X3=one or more non-universal bases.

12. A method of tagging a double-stranded nucleic acid of interest, comprising:
(a) contacting the nucleic acid of interest with a double stranded nucleic acid adaptor of claim 1; and
(b) ligating the adaptor to the nucleic acid of interest,
wherein the adaptor is ligated to the nucleic acid of interest at the 3' end of the first strand of the adaptor but is not ligated at the 5' end of the second strand of the adaptor.

13. The method of claim 12, wherein the method further comprises a step of extending the nucleic acid of interest in a 5' to 3' direction over the ligated strand of the adaptor to generate a random tag.

14. The method of claim 12, wherein an adaptor is ligated at each 5' end of the nucleic acid of interest and the method further comprises a step of extending the nucleic acid of interest in a 5' to 3' direction over the ligated strand of both the adaptors to generate a random tag at each end of the nucleic acid of interest.

15. A method for determining the sequence of a nucleic acid of interest, the method comprising:
(a) contacting the nucleic acid of interest with an adaptor of claim 1;
(b) ligating the adaptor to one or both ends of the nucleic acid of interest;
(c) extending the nucleic acid of interest over the ligated adaptor to generate a random tag on the nucleic acid of interest;
(d) amplifying the tagged nucleic acid of interest; and
(e) determining the sequence of the nucleic acid of interest.

* * * * *

SEQUENCE LISTING

```
<160> NUMBER OF SEQ ID NOS: 35

<210> SEQ ID NO 1
<211> LENGTH: 24
<212> TYPE: DNA
<213> ORGANISM: Artificial Sequence
<220> FEATURE:
<223> OTHER INFORMATION: Full-length adaptor sense strand

<400> SEQUENCE: 1
gcacctcacc tcagcatctg actc                                            24

<210> SEQ ID NO 2
<211> LENGTH: 25
<212> TYPE: DNA
<213> ORGANISM: Artificial Sequence
<220> FEATURE:
<223> OTHER INFORMATION: Full length adaptor antisense strand
<220> FEATURE:
<221> NAME/KEY: misc_feature
<222> LOCATION: (9)..(9)
<223> OTHER INFORMATION: n is I
<220> FEATURE:
<221> NAME/KEY: misc_feature
<222> LOCATION: (12)..(12)
<223> OTHER INFORMATION: n is I
<220> FEATURE:
<221> NAME/KEY: misc_feature
<222> LOCATION: (15)..(15)
<223> OTHER INFORMATION: n is I
<220> FEATURE:
<221> NAME/KEY: misc_feature
<222> LOCATION: (20)..(20)
<223> OTHER INFORMATION: n is I

<400> SEQUENCE: 2
gagtcagang cngangtgan gtgct                                           25

<210> SEQ ID NO 3
<211> LENGTH: 21
<212> TYPE: DNA
<213> ORGANISM: Artificial Sequence
<220> FEATURE:
```

```
<223> OTHER INFORMATION: Full length adaptor sense strand
<220> FEATURE:
<221> NAME/KEY: misc_feature
<222> LOCATION: (1)..(1)
<223> OTHER INFORMATION: n is I
<220> FEATURE:
<221> NAME/KEY: misc_feature
<222> LOCATION: (3)..(3)
<223> OTHER INFORMATION: n is I
<220> FEATURE:
<221> NAME/KEY: misc_feature
<222> LOCATION: (5)..(5)
<223> OTHER INFORMATION: n is I
<220> FEATURE:
<221> NAME/KEY: misc_feature
<222> LOCATION: (7)..(7)
<223> OTHER INFORMATION: n is I
<220> FEATURE:
<221> NAME/KEY: misc_feature
<222> LOCATION: (9)..(9)
<223> OTHER INFORMATION: n is I
<220> FEATURE:
<221> NAME/KEY: misc_feature
<222> LOCATION: (11)..(11)
<223> OTHER INFORMATION: n is I
<220> FEATURE:
<221> NAME/KEY: misc_feature
<222> LOCATION: (13)..(13)
<223> OTHER INFORMATION: n is I
<220> FEATURE:
<221> NAME/KEY: misc_feature
<222> LOCATION: (15)..(15)
<223> OTHER INFORMATION: n is I

<400> SEQUENCE: 3
ngnantncna ngnancggag t                                            21

<210> SEQ ID NO 4
<211> LENGTH: 20
<212> TYPE: DNA
<213> ORGANISM: Artificial Sequence
<220> FEATURE:
<223> OTHER INFORMATION: Full length adaptor antisense strand

<400> SEQUENCE: 4
ctccgatcca tcgcaatccc                                              20

<210> SEQ ID NO 5
<211> LENGTH: 33
<212> TYPE: DNA
<213> ORGANISM: Artificial Sequence
<220> FEATURE:
<223> OTHER INFORMATION: Assymetric Y stem adaptor sense strand

<400> SEQUENCE: 5
acactctttc cctacacgac gctcttccga tct                               33

<210> SEQ ID NO 6
<211> LENGTH: 31
<212> TYPE: DNA
<213> ORGANISM: Artificial Sequence
<220> FEATURE:
<223> OTHER INFORMATION: Assymetric Y stem adaptor antisense strand

<400> SEQUENCE: 6
gatcggaaga gcacacgtct gaactccagt c                                 31

<210> SEQ ID NO 7
<211> LENGTH: 70
<212> TYPE: DNA
<213> ORGANISM: Artificial Sequence
```

```
<220> FEATURE:
<223> OTHER INFORMATION: i5 PCR primer
<220> FEATURE:
<221> NAME/KEY: misc_feature
<222> LOCATION: (30)..(37)
<223> OTHER INFORMATION: n is a, c, g, or t

<400> SEQUENCE: 7
aatgatacgg cgaccaccga gatctacacn nnnnnnnaca ctctttccct acacgacgct    60
cttccgatct                                                          70

<210> SEQ ID NO 8
<211> LENGTH: 66
<212> TYPE: DNA
<213> ORGANISM: Artificial Sequence
<220> FEATURE:
<223> OTHER INFORMATION: i7 PCR primer
<220> FEATURE:
<221> NAME/KEY: misc_feature
<222> LOCATION: (25)..(32)
<223> OTHER INFORMATION: n is a, c, g, or t

<400> SEQUENCE: 8
caagcagaag acggcatacg agatnnnnnn nngtgactgg agttcagacg tgtgctcttc    60
cgatct                                                              66

<210> SEQ ID NO 9
<211> LENGTH: 24
<212> TYPE: DNA
<213> ORGANISM: Artificial Sequence
<220> FEATURE:
<223> OTHER INFORMATION: Full length adaptor sense strand
<220> FEATURE:
<221> NAME/KEY: misc_feature
<222> LOCATION: (1)..(1)
<223> OTHER INFORMATION: n is I
<220> FEATURE:
<221> NAME/KEY: misc_feature
<222> LOCATION: (5)..(5)
<223> OTHER INFORMATION: n is I
<220> FEATURE:
<221> NAME/KEY: misc_feature
<222> LOCATION: (7)..(8)
<223> OTHER INFORMATION: n is I
<220> FEATURE:
<221> NAME/KEY: misc_feature
<222> LOCATION: (10)..(10)
<223> OTHER INFORMATION: n is I
<220> FEATURE:
<221> NAME/KEY: misc_feature
<222> LOCATION: (13)..(14)
<223> OTHER INFORMATION: n is I
<220> FEATURE:
<221> NAME/KEY: misc_feature
<222> LOCATION: (16)..(16)
<223> OTHER INFORMATION: n is I
<220> FEATURE:
<221> NAME/KEY: misc_feature
<222> LOCATION: (18)..(18)
<223> OTHER INFORMATION: n is I
<220> FEATURE:
<221> NAME/KEY: misc_feature
<222> LOCATION: (21)..(21)
<223> OTHER INFORMATION: n is I

<400> SEQUENCE: 9
nacgngnngn cgnncnanag nagt                                          24

<210> SEQ ID NO 10
<211> LENGTH: 23
<212> TYPE: DNA
```

```
<213> ORGANISM: Artificial Sequence
<220> FEATURE:
<223> OTHER INFORMATION: Full length adaptor antisense strand

<400> SEQUENCE: 10
ctcctatcga acgccaaccc gtc                                            23

<210> SEQ ID NO 11
<211> LENGTH: 24
<212> TYPE: DNA
<213> ORGANISM: Artificial Sequence
<220> FEATURE:
<223> OTHER INFORMATION: Full length adaptor sense strand
<220> FEATURE:
<221> NAME/KEY: misc_feature
<222> LOCATION: (2)..(2)
<223> OTHER INFORMATION: n is I
<220> FEATURE:
<221> NAME/KEY: misc_feature
<222> LOCATION: (4)..(4)
<223> OTHER INFORMATION: n is I
<220> FEATURE:
<221> NAME/KEY: misc_feature
<222> LOCATION: (6)..(6)
<223> OTHER INFORMATION: n is I
<220> FEATURE:
<221> NAME/KEY: misc_feature
<222> LOCATION: (8)..(8)
<223> OTHER INFORMATION: n is I
<220> FEATURE:
<221> NAME/KEY: misc_feature
<222> LOCATION: (10)..(10)
<223> OTHER INFORMATION: n is I
<220> FEATURE:
<221> NAME/KEY: misc_feature
<222> LOCATION: (12)..(12)
<223> OTHER INFORMATION: n is I
<220> FEATURE:
<221> NAME/KEY: misc_feature
<222> LOCATION: (14)..(14)
<223> OTHER INFORMATION: n is I
<220> FEATURE:
<221> NAME/KEY: misc_feature
<222> LOCATION: (16)..(16)
<223> OTHER INFORMATION: n is I
<220> FEATURE:
<221> NAME/KEY: misc_feature
<222> LOCATION: (18)..(18)
<223> OTHER INFORMATION: n is I
<220> FEATURE:
<221> NAME/KEY: misc_feature
<222> LOCATION: (20)..(20)
<223> OTHER INFORMATION: n is I

<400> SEQUENCE: 11
gnangnantn gnananancn gagt                                           24

<210> SEQ ID NO 12
<211> LENGTH: 23
<212> TYPE: DNA
<213> ORGANISM: Artificial Sequence
<220> FEATURE:
<223> OTHER INFORMATION: Full length adaptor antisense strand

<400> SEQUENCE: 12
ctccgatcta tcccaatccc tac                                            23

<210> SEQ ID NO 13
<211> LENGTH: 24
<212> TYPE: DNA
<213> ORGANISM: Artificial Sequence
<220> FEATURE:
<223> OTHER INFORMATION: Full length adaptor sense strand
```

```
<220> FEATURE:
<221> NAME/KEY: misc_feature
<222> LOCATION: (4)..(4)
<223> OTHER INFORMATION: n is I
<220> FEATURE:
<221> NAME/KEY: misc_feature
<222> LOCATION: (6)..(7)
<223> OTHER INFORMATION: n is I
<220> FEATURE:
<221> NAME/KEY: misc_feature
<222> LOCATION: (9)..(10)
<223> OTHER INFORMATION: n is I
<220> FEATURE:
<221> NAME/KEY: misc_feature
<222> LOCATION: (12)..(12)
<223> OTHER INFORMATION: n is I
<220> FEATURE:
<221> NAME/KEY: misc_feature
<222> LOCATION: (14)..(14)
<223> OTHER INFORMATION: n is I
<220> FEATURE:
<221> NAME/KEY: misc_feature
<222> LOCATION: (16)..(16)
<223> OTHER INFORMATION: n is I
<220> FEATURE:
<221> NAME/KEY: misc_feature
<222> LOCATION: (18)..(18)
<223> OTHER INFORMATION: n is I
<220> FEATURE:
<221> NAME/KEY: misc_feature
<222> LOCATION: (22)..(22)
<223> OTHER INFORMATION: n is I

<400> SEQUENCE: 13
cgcngnngnn cnangngncg gngt                                              24

<210> SEQ ID NO 14
<211> LENGTH: 23
<212> TYPE: DNA
<213> ORGANISM: Artificial Sequence
<220> FEATURE:
<223> OTHER INFORMATION: Full length adaptor antisense strand

<400> SEQUENCE: 14
caccgaccca tcgcacaccc gcg                                               23

<210> SEQ ID NO 15
<211> LENGTH: 24
<212> TYPE: DNA
<213> ORGANISM: Artificial Sequence
<220> FEATURE:
<223> OTHER INFORMATION: Full length adaptor sense strand
<220> FEATURE:
<221> NAME/KEY: misc_feature
<222> LOCATION: (3)..(3)
<223> OTHER INFORMATION: n is I
<220> FEATURE:
<221> NAME/KEY: misc_feature
<222> LOCATION: (5)..(5)
<223> OTHER INFORMATION: n is I
<220> FEATURE:
<221> NAME/KEY: misc_feature
<222> LOCATION: (8)..(8)
<223> OTHER INFORMATION: n is I
<220> FEATURE:
<221> NAME/KEY: misc_feature
<222> LOCATION: (10)..(10)
<223> OTHER INFORMATION: n is I
<220> FEATURE:
<221> NAME/KEY: misc_feature
<222> LOCATION: (12)..(13)
<223> OTHER INFORMATION: n is I
<220> FEATURE:
<221> NAME/KEY: misc_feature
<222> LOCATION: (15)..(15)
```

```
<223> OTHER INFORMATION: n is I
<220> FEATURE:
<221> NAME/KEY: misc_feature
<222> LOCATION: (17)..(18)
<223> OTHER INFORMATION: n is I
<220> FEATURE:
<221> NAME/KEY: misc_feature
<222> LOCATION: (23)..(23)
<223> OTHER INFORMATION: n is I

<400> SEQUENCE: 15
aangnganan cnntngnncg gant                                                24

<210> SEQ ID NO 16
<211> LENGTH: 23
<212> TYPE: DNA
<213> ORGANISM: Artificial Sequence
<220> FEATURE:
<223> OTHER INFORMATION: Full length adaptor antisense strand

<400> SEQUENCE: 16
ctccgaacca ccgctatccc ctt                                                 23

<210> SEQ ID NO 17
<211> LENGTH: 25
<212> TYPE: DNA
<213> ORGANISM: Artificial Sequence
<220> FEATURE:
<223> OTHER INFORMATION: Full length adaptor sense strand

<400> SEQUENCE: 17
gcacctcacc tcagcatcga ctgag                                               25

<210> SEQ ID NO 18
<211> LENGTH: 26
<212> TYPE: DNA
<213> ORGANISM: Artificial Sequence
<220> FEATURE:
<223> OTHER INFORMATION: Full length adaptor antisense strand
<220> FEATURE:
<221> NAME/KEY: misc_feature
<222> LOCATION: (10)..(10)
<223> OTHER INFORMATION: n is I
<220> FEATURE:
<221> NAME/KEY: misc_feature
<222> LOCATION: (13)..(13)
<223> OTHER INFORMATION: n is I
<220> FEATURE:
<221> NAME/KEY: misc_feature
<222> LOCATION: (16)..(16)
<223> OTHER INFORMATION: n is I
<220> FEATURE:
<221> NAME/KEY: misc_feature
<222> LOCATION: (21)..(21)
<223> OTHER INFORMATION: n is I

<400> SEQUENCE: 18
ctcagtcgan gcngangtga ngtgct                                              26

<210> SEQ ID NO 19
<211> LENGTH: 26
<212> TYPE: DNA
<213> ORGANISM: Artificial Sequence
<220> FEATURE:
<223> OTHER INFORMATION: Full length adaptor sense strand

<400> SEQUENCE: 19
gcacctcacc tcagcatcta cagtct                                              26
```

```
<210> SEQ ID NO 20
<211> LENGTH: 27
<212> TYPE: DNA
<213> ORGANISM: Artificial Sequence
<220> FEATURE:
<223> OTHER INFORMATION: Full length adaptor antisense strand
<220> FEATURE:
<221> NAME/KEY: misc_feature
<222> LOCATION: (11)..(11)
<223> OTHER INFORMATION: n is I
<220> FEATURE:
<221> NAME/KEY: misc_feature
<222> LOCATION: (14)..(14)
<223> OTHER INFORMATION: n is I
<220> FEATURE:
<221> NAME/KEY: misc_feature
<222> LOCATION: (17)..(17)
<223> OTHER INFORMATION: n is I
<220> FEATURE:
<221> NAME/KEY: misc_feature
<222> LOCATION: (22)..(22)
<223> OTHER INFORMATION: n is I

<400> SEQUENCE: 20
agactgtaga ngcngangtg angtgct                                          27

<210> SEQ ID NO 21
<211> LENGTH: 27
<212> TYPE: DNA
<213> ORGANISM: Artificial Sequence
<220> FEATURE:
<223> OTHER INFORMATION: Full length adaptor sense strand

<400> SEQUENCE: 21
gcacctcacc tcagcatcaa tgtcaga                                          27

<210> SEQ ID NO 22
<211> LENGTH: 28
<212> TYPE: DNA
<213> ORGANISM: Artificial Sequence
<220> FEATURE:
<223> OTHER INFORMATION: Full length adaptor antisense strand
<220> FEATURE:
<221> NAME/KEY: misc_feature
<222> LOCATION: (12)..(12)
<223> OTHER INFORMATION: n is I
<220> FEATURE:
<221> NAME/KEY: misc_feature
<222> LOCATION: (15)..(15)
<223> OTHER INFORMATION: n is I
<220> FEATURE:
<221> NAME/KEY: misc_feature
<222> LOCATION: (18)..(18)
<223> OTHER INFORMATION: n is I
<220> FEATURE:
<221> NAME/KEY: misc_feature
<222> LOCATION: (23)..(23)
<223> OTHER INFORMATION: n is I

<400> SEQUENCE: 22
tctgacattg angcngangt gangtgct                                         28

<210> SEQ ID NO 23
<211> LENGTH: 41
<212> TYPE: DNA
<213> ORGANISM: Artificial Sequence
<220> FEATURE:
<223> OTHER INFORMATION: Exstension adaptor and NAOI molecule sequences

<400> SEQUENCE: 23
tgcgtagcgg tgcaagcagc cgtacatgag accgctacgc a                          41
```

```
<210> SEQ ID NO 24
<211> LENGTH: 41
<212> TYPE: DNA
<213> ORGANISM: Artificial Sequence
<220> FEATURE:
<223> OTHER INFORMATION: Extension adaptor and NAOI sequence

<400> SEQUENCE: 24
tgttagctag tgcatgcagc cgtacatgag accgctacgc a                    41

<210> SEQ ID NO 25
<211> LENGTH: 41
<212> TYPE: DNA
<213> ORGANISM: Artificial Sequence
<220> FEATURE:
<223> OTHER INFORMATION: Extension adaptor and NAOI sequence

<400> SEQUENCE: 25
tgaatgatcg tgcatgcagc cgtacatgag accgctacgc a                    41

<210> SEQ ID NO 26
<211> LENGTH: 41
<212> TYPE: DNA
<213> ORGANISM: Artificial Sequence
<220> FEATURE:
<223> OTHER INFORMATION: Extension adaptor and NAOI sequence

<400> SEQUENCE: 26
tgccgatagg tgcatgcagc cgtacatgag accgctacgc a                    41

<210> SEQ ID NO 27
<211> LENGTH: 41
<212> TYPE: DNA
<213> ORGANISM: Artificial Sequence
<220> FEATURE:
<223> OTHER INFORMATION: Extension adaptor and NAOI sequence

<400> SEQUENCE: 27
tgcgtagcgg tgcaagcagc cgtacatgag accgctacgc a                    41

<210> SEQ ID NO 28
<211> LENGTH: 40
<212> TYPE: DNA
<213> ORGANISM: Artificial Sequence
<220> FEATURE:
<223> OTHER INFORMATION: Extension adaptor and NAOI sequence

<400> SEQUENCE: 28
tggtagcatg tgcagaagcc gtagatgaga cttgacgaca                      40

<210> SEQ ID NO 29
<211> LENGTH: 41
<212> TYPE: DNA
<213> ORGANISM: Artificial Sequence
<220> FEATURE:
<223> OTHER INFORMATION: Extension adaptor and NAOI sequence

<400> SEQUENCE: 29
tgtgatcatg tgcatgcagc cgtagatgag acttgacgac a                    41

<210> SEQ ID NO 30
<211> LENGTH: 41
<212> TYPE: DNA
<213> ORGANISM: Artificial Sequence
<220> FEATURE:
<223> OTHER INFORMATION: Extension adaptor and NAOI sequence
```

```
<400> SEQUENCE: 30
tgttagctag tgcatgcagc cgtagatgag acttgacgac a                           41

<210> SEQ ID NO 31
<211> LENGTH: 41
<212> TYPE: DNA
<213> ORGANISM: Artificial Sequence
<220> FEATURE:
<223> OTHER INFORMATION: Extension adaptor and NAOI sequence

<400> SEQUENCE: 31
tgcgtatcgg tgcatgcagc cgtagatgag acttgacgac a                           41

<210> SEQ ID NO 32
<211> LENGTH: 41
<212> TYPE: DNA
<213> ORGANISM: Artificial Sequence
<220> FEATURE:
<223> OTHER INFORMATION: Extension adaptor and NAOI sequence

<400> SEQUENCE: 32
tgagtgatcg tgcatgcagc cgtagatgag acttgacgac a                           41

<210> SEQ ID NO 33
<211> LENGTH: 41
<212> TYPE: DNA
<213> ORGANISM: Artificial Sequence
<220> FEATURE:
<223> OTHER INFORMATION: Extension adaptor and NAOI sequence

<400> SEQUENCE: 33
tgcttagcgg tgcatgcagc cgtagatgag acttgacgac a                           41

<210> SEQ ID NO 34
<211> LENGTH: 19
<212> TYPE: DNA
<213> ORGANISM: Artificial sequence
<220> FEATURE:
<223> OTHER INFORMATION: synthetic sequence

<400> SEQUENCE: 34
gcatgcagcc gtacatgag                                                    19

<210> SEQ ID NO 35
<211> LENGTH: 19
<212> TYPE: DNA
<213> ORGANISM: Artificial sequence
<220> FEATURE:
<223> OTHER INFORMATION: synthetic sequence

<400> SEQUENCE: 35
gcatgcagcc gtagatgag                                                    19
```